US006361768B1

(12) United States Patent
Galleguillos et al.

(10) Patent No.: US 6,361,768 B1
(45) Date of Patent: Mar. 26, 2002

(54) HYDROPHILIC AMPHOLYTIC POLYMER

(75) Inventors: Ramiro Galleguillos, Hudson; Jodi A. Budrevich, Cuyahoga Falls; Joseph A. Chiarelli, Broadview Heights; Harinath B. Bathina, Hudson; Zahid Amjad, Brecksville, all of OH (US)

(73) Assignee: PMD Holdings Corp., Brecksville, OH (US)

( * ) Notice: Subject to any disclaimer, the term of this patent is extended or adjusted under 35 U.S.C. 154(b) by 0 days.

(21) Appl. No.: 09/222,495

(22) Filed: Dec. 29, 1998

(51) Int. Cl.[7] .............................. A61K 7/06; A61K 7/11; B05D 3/02; C08F 20/26

(52) U.S. Cl. ................... 424/70.12; 424/70.12; 424/70.13; 424/70.14; 424/70.22; 424/70.24; 424/70.27; 424/70.31; 424/78.08; 424/78.1; 424/401; 424/49; 8/115.6; 427/385.5; 526/318.42; 526/318.44; 526/318.5

(58) Field of Search ................ 424/70.16, 70.21, 424/78.35, 70.12, 70.13, 70.14, 70.22, 70.24, 70.27, 70.31, 78.08, 78.1, 401, 49; 8/115.6; 427/385.5; 526/318.42, 318.44, 318.5

(56) References Cited

U.S. PATENT DOCUMENTS

| | | | | |
|---|---|---|---|---|
| 2,205,882 A | * | 6/1940 | Graves | 526/317 |
| 3,929,678 A | | 12/1975 | Laughlin et al. | |
| 3,990,459 A | * | 11/1976 | Papantoniou | 424/70.16 |
| 4,028,295 A | | 6/1977 | Loshaek | |
| 4,076,921 A | | 2/1978 | Stol et al. | |
| 4,486,489 A | * | 12/1984 | George | 526/318.42 |
| 4,889,637 A | | 12/1989 | Amjad et al. | |
| 4,904,749 A | | 2/1990 | Brusky et al. | |
| 5,073,612 A | * | 12/1991 | Irie et al. | 526/318.42 |
| 5,075,399 A | | 12/1991 | Ahmed et al. | |
| 5,100,657 A | | 3/1992 | Ansher-Jackson et al. | |
| 5,116,921 A | | 5/1992 | Hsieh | |
| 5,130,391 A | | 7/1992 | Ahmed et al. | |
| 5,159,034 A | | 10/1992 | Tazi | |
| 5,216,098 A | | 6/1993 | Ahmed et al. | |
| 5,219,559 A | | 6/1993 | Kopolow | |
| 5,262,244 A | | 11/1993 | Faust et al. | |
| 5,286,827 A | | 2/1994 | Ahmed | |
| 5,288,814 A | | 2/1994 | Long, II et al. | |
| 5,321,110 A | | 6/1994 | Shih | |
| 5,362,815 A | | 11/1994 | Shih et al. | |
| 5,362,830 A | | 11/1994 | Chuang et al. | |
| 5,603,926 A | | 2/1997 | Matsumoto et al. | |
| 5,608,021 A | | 3/1997 | Uchiyama et al. | |

(List continued on next page.)

FOREIGN PATENT DOCUMENTS

| | | |
|---|---|---|
| DE | 9016661 | 2/1991 |
| EP | 479245 | 4/1992 |
| FR | 2393011 | 12/1978 |

OTHER PUBLICATIONS

Acta Phar. Tehnol., Robert et al., "Experimental Method for Bioadhesive Testing of Various Polymers", vol. 3492), pp. 95–98, 1988.
Journal of Pharmaceutical Sciences, Burt et al., "Ion–Exchange Resins as Potential Phosphate–Binding Agents for Renal Failure Patients: Effect of the Physicochemical Properties of Resins on Phosphate and Bile Salt Binding", vol. 76, No. 5, pp. 379–383, May 1987.
Eur. J. Pharm. Biopharm., Michael J. Tobyn et al., "Factors Affecting in Vitro Gastric Mucoadhesion I. Test Conditions and Instrumental Parameters", 41(4), pp. 234–241, 1995.
International Journal of Pharmaceutics, H. Blanco–Fuente et al., "Tanned Leather: A Good Model for Determining Hydrogels Bioadhesion", vol. 138, pp. 103–112, 1996.
Journal of Controlled Release, G. Borcard et al., "The Potential of Mucoadhesive Polymers in Enhancing Intestinal Peptide Drug Absorption. III: Effects of Chitosan–Glutamate and Carbomer on Epithelial Tight Junctions in Vitro", vol. 39, pp. 131–138, 1996.
Eur. J. Pharm. Biopharm., Michael J. Tobyn et al., "Factors Affecting in Vitro Gastric Mucoadhesion I. Test Conditions and Instrumental Parameters", 41(4), pp. 234–241, 1995 (no month).
International Journal of Pharmaceutics, H. Blanco–Fuente et al, "Tanned Leather: A Good Model for Determing Hydrogels Bioadhesion", vol. 138, pp. 103–112, 1996 (no month).
Acta Phar. Tehnol., Robert et al., "Experimental Method for Bioadhesive Testing of Various Polymers", vol. 34(2), pp. 95–98, 1988 (no month).
Journal of Pharmaceutical Sciences, Burt et al., "Ion–Exchange Resins as Potential Phosphate–Binding Agents for Renal Failure Patients: Effect of the Physicochemical Properties of Resins on Phosphate and Bile Salt Binding", vol. 76, No. 5, pp. 379–383, May, 1987.
Journal of Controlled Release, G. Borcard et al., The Potential of Mucoadhesive Polymers in Enhancing Intestinal Peptide Drug Absorption. III: Effects of Chitosan–Glutamate and Carbomer on Epithelial Tight Junctions in Vitro, vol. 39, pp. 131–136, 1996 (no month).

*Primary Examiner*—Thurman K. Page
*Assistant Examiner*—Humera N. Sheikh
(74) *Attorney, Agent, or Firm*—George W. Moxon, II; Hudak & Shunk Co., L.P.A.

(57) ABSTRACT

A novel hydrophilic ampholytic polymer synthesized by reacting polymerizable amino and carboxy functional ethylenically unsaturated monomers, together with a non-ionic hydrophilic monomer, to provide a polymer having a glass transition temperature ($T_g$) above about 50° C., and optionally hydrophobic monomer(s), and cross-linking monomer (s). The copolymer is precipitated from a polymerization media which includes a suitable organic solvent. The resulting copolymer is in the form of a fine powder, with submicron particle size. As such it is suitable for use as a thickener or rheology modifier in personal care formulations, such as shampoo, conditioner, and the like, as a bioadhesive, and for other pharmaceutical applications.

54 Claims, No Drawings

U.S. PATENT DOCUMENTS

| | | |
|---|---|---|
| 5,609,865 A | 3/1997 | Liu et al. |
| 5,645,859 A | 7/1997 | Chaudhuri et al. |
| 5,654,385 A | 8/1997 | Tseng et al. |
| 5,663,258 A | 9/1997 | Zhong et al. |
| 5,667,775 A | 9/1997 | Holmes-Farley et al. |
| 5,744,155 A | 4/1998 | Friedman et al. |
| 5,948,396 A * | 9/1999 | Das et al. ................ 424/70.16 |

* cited by examiner

HYDROPHILIC AMPHOLYTIC POLYMER

BACKGROUND OF THE INVENTION

The present invention is directed to a novel, hydrophilic, ampholytic polymer. Hydrophilic polymers readily associate with, have an affinity for, and dissolve in water. Ampholytic polymer(s), or polyampholyte(s), are polymer(s) having both cationic and anionic groups. The polymers of the present invention have utility as rheology modifiers in cationic and low pH (acidic) systems, as bioadhesives, as agents in the removal of bile salts and for enzyme inhibition, and as phosphate binding agents.

Ampholytic polymers are known. For example, U.S. Pat. Nos. 5,286,827; 5,216,098; 5,130,391; 5,116,921; and 5,075,399 teach superabsorbent crosslinked ampholytic ion pair copolymers, which are in powder form for incorporation into baby diapers. The ampholytic nature of the polymer facilitates the absorption of urine.

Polymers which are used as rheology modifiers or thickeners include non-ionic, cationic, anionic, and associative type thickeners. Non-ionic polymers include, for example, naturally occurring and chemically modified gums. Cationic polymers tend to be nonionic polymers, such as the natural gums which have been quaternized to make them compatible with cationic systems, although synthetic polymers are known, such as U.S. Pat. Nos 5,603,926 (Matsumoto et al) and 5,608,021(Uchiyama et al), which teach polymers from acrylic monomers having amino groups, and U.S. Pat. No. 5,321,110 (J. S. Shih), which teaches a vinyl pyrrolidone based polymer that includes an acrylic monomer having an amino group, which is quaternized to make it cationic. Anionic polymers, or polyelectrolytes include polycarboxylic acids, such as polyacrylic acid and the like. Associative polymer thickeners include hydrophobically-modified variations of non-ionic and ionic polymers, which function by "self-association" when dissolved in aqueous systems.

Unfortunately, however, the aforementioned conventional water-soluble polymers suffer from many serious deficiencies or limitations in actual use. For example, polymers are often added to personal care, medical, pharmaceutical, and household products to modify, the physical form, function, aesthetics and rheology properties of the formulations so that the product is delivered in a convenient form for application by the end user. Shampoos, for example, are theologically modified to allow a portion of the formulation to be readily poured from a container and yet be retained in the palm of the user's hand without flowing further. But, their use may lead to or be impeded by formulation problems, such as unfavorable interactions with other ingredients of the formulations. Commercial hair care and personal care formulations, in particular, often contain cationic and amphoteric surfactants, as well as salts, other polymers, non-aqueous solvents, oils, colorants, peroxides, acids, and bases. Hair conditioning compositions, for example, frequently include cationic surfactants as conditioning agents for improving conditioning and detangling of the hair. See, for example, U.S. Pat. No. 5,100,657 which discloses quaternary ammonium-containing cationic surfactants, such as dialkyldimethylammonium chlorides and salts of fatty amines. The interaction of the thickening polymer with these formulation ingredients results in substantial viscosity reduction, formation of insoluble complexes or produce "stringy" or viscous rheology. The natural cellulosic gums, even if modified to make them cationic thickeners, still tend to be unacceptable in terms of their rheology, which will include stringy, and elastic rheologies, which are esthetically and functionally undesirable in a final formulation.

In addition, cations, from, e.g., cationic and amphoteric surfactants, are commonly employed in the formulations of cosmetic, personal care, household, textiles paper coating and printing, pharmaceutical and other products such as shampoos, conditioners, hair gels, mousses, hand cleaning soaps, oral delivery compositions such as syrups, as carriers for drugs in tablet form, in dental products, such as toothpaste and the like. A problem is that surfactants in a system may tend to disrupt the thickening mechanism, so that the thickeners tend to lose their viscosity in the presence of the surfactants typically used in cosmetic compositions. Anionic polymeric thickeners which are known to thicken and maintain the viscosity of cosmetic, and other formulations in an efficient and aesthetic manner, do not maintain their viscosity in the presence of cationic surfactants. Some nonionic thickeners can maintain the viscosity of cationic or amphoteric surfactant-containing formulations, however they have the problem that they produce elastic or "stringy" formulations which tend to flow as a single mass and are aesthetically unacceptable.

Hydrophilic polymers have been used for many years in bioadhesion systems in dentistry, orthopaedics, drug delivery, and surgical applications. The term "bioadhesion" has been used to describe phenomena related to the ability of some synthetic and biological macromolecules and hydrocolloids to adhere to biological tissues. For drug delivery, natural and synthetic bioadhesive polymers of different ionic charge (neutral, anionic, or cationic) are selected for their bioadhesive properties. The pH of the body varies throughout the digestive system. The stomach, for example, has a pH of around 1 to 2, whereas the intestinal tract has a pH in the range of 5 to 8. By selecting polymers with suitable ionic charge, the site of adsorption can be varied according to the pH. More recently, there has also been a significant interest in the use of hydrophilic polymers as bioadhesive materials in other areas, such as soft tissue-based artificial replacement and controlled release systems for local release of bioactive agents. Such applications include systems for release of drugs in the buccal or nasal cavities and for intestinal or rectal administration. For example, Blanco-Fuente et al. discloses the bioadhesive properties of natural cellulosic and crosslinked acrylic acid polymers. (Int. J. Pharm. 138, pp. 103–112 (1996)). The bioadhesive properties of poly N-vinylpyrrolidone (PNVP), and poly hydroxyethylmethacrylate (PHEMA) have been reported by Robert et al. (Acta Phar. Tehnol., 34 (2) pp. 95–98 (1988)). Natural cationic materials, such as chitosan have also been found to exhibit good bioadhesive properties. However, because such polymers are sometimes incompatible with certain active agents, such as medicines, which are to be delivered, there exists a need for polymers having bioadhesive properties which will provide that compatibility and perform at the desired pH levels.

In some cases, hydrophilic polymer systems have been used as therapeutic agents themselves. Burt et al. (J. Pharm. Sci. 76 (5), pp. 379–383 (1987)) discloses the use of an anion-exchange resin for binding phosphate in the blood. Phosphorus is present in the many sources of protein foods. In people with healthy kidneys, excess phosphorus is excreted in their urine. However, in patients with chronic renal failure, the kidneys are unable to maintain a delicate balance between phosphorus and calcium levels in the blood. Phosphorus is not excreted efficiently and thus builds up in the blood, a condition called hyperphosphatemia. Uncontrolled hyperphosphatemia causes a calcium-phosphate complex to precipitate in soft tissues, such as arteries, essentially turning them into bone. Hyperphosphatemia also causes increased secretion of the parathyroid hormone, which in turn causes bone degradation. Because a reduced dietary amount of phosphate is generally inadequate in reversing hyperphosphatemia, oral administration of certain phosphate binders has been suggested. Phosphate binders include calcium or aluminum salts which complex with phosphate to form insoluble calcium and aluminum salts. The long use of calcium and aluminum salts leads to hypercalcemia and aluminum toxicity.

Anion-exchange resins, some in the chloride form, have been recently suggested for use in binding phosphate and in the treatment of hyperphosphatemia. However, due their poor binding efficiency, high dosages are needed for a significant reduction in the absorbed phosphate. U.S. Pat. No. 5,667,775, for example, discloses using amine-containing crosslinked homopolymers for binding phosphate. Poly (allylamine) crosslinked with epichlorohydrin has shown some effectiveness as a phosphate binder. However, such compositions tend to be unsuited to oral administration. They are not readily absorbed into the bloodstream from the digestive system.

Another area of potential use of polymers is in absorption enhancers. For drugs that are administered orally, the drug must be transported from the digestive system into the blood stream. A membrane separates the intestinal tract from the blood stream. There are a number of ways in which materials, such as drugs pass through the membrane. In one transport system the material passes directly through the outer layer of cells, the epithelial layer. In a second system, receptors in the cells attract the material and push it through. In a third system, the material passes between cells. In this latter, "paracellular" transport mechanism, the normally tight junction between the cells is opened in order for the material to pass through. Some compounds are known to influence the absorption of drugs by assisting the opening of these junctions. Several different types of absorption enhancers, such as surfactants, fatty acids, chelating agents, and polymeric (anionic and cationic) materials have been tried with limited success. For example, Borchart et al. discloses the use of chitosan glutanate (a naturally occurring cationic polysaccharide) and crosslinked polyacrylic acids, such as Carbopol® 934, as absorption enhancers for insulin. (G. Borcard et al., J. Controlled Release 29, p. 39 (1996)).

The present invention provides for a new hydrophilic ampholylic polymer which overcomes the above-referenced problems, and others.

SUMMARY OF THE INVENTION

The present invention is a novel, hydrophilic ampholytic polymer or copolymer, having both cationic and anionic groups, formed by copolymerization of amino-functional and carboxy-functional ethylenically unsaturated monomers together with a hydrophilic, non-ionic monomer of high glass transition temperature ($T_g$) and, optionally, a cross linking monomer. The copolymer dissolves readily in water and builds up viscosity when added to water-based compositions. It is also useful as a bioadhesive and for other pharmaceutical applications.

In accordance with another aspect of the present invention, a method of preparing a hydrophilic ampholytic copolymer is provided by copolymerizing the requisite monomer components.

The new polymer is compatible with cationic materials, such as quaternized surfactants and is particularly suited to use in personal care compositions, such as shampoos, hair conditioners, hair gels, and various other cosmetic compositions where cationic surfactants are frequently used. It should be appreciated, however, that the material is also applicable to use in a wide range of water-based compositions for modifying the rheology of the composition or increasing viscosity, such as household products, cleaning compositions, toothpaste, pharmaceutical products, and the like. The material also finds application in drug delivery compositions and in the selective removal of ions, such as phosphates, from body fluids.

In accordance with other aspects of the present invention, the copolymer is compatible with acids and may be incorporated into acidic formulations, such as those containing organic and inorganic acids at low pH, shampoo and conditioning formulations, including those containing cationic surfactants, fabric softeners, personal care and household cleaning formulations, and pharmaceutical products.

One advantage of the present invention is the provision of a polymeric thickener which is compatible with high levels of cationic surfactants.

Another advantage of the present invention is that the polymer readily disperses in aqueous formulations and is capable of thickening aqueous formulations over a wide range of pH.

Yet another advantage of the present invention is that the polymer can be used in combination with anionic, cationic and non ionic systems.

A still further advantage of the present invention is that the polymer is amino functionalized and can deliver conditioning, anti-static, and improved adhesion to biosubstrates, such as hair, skin, and internal membranes of the gastrointestinal system, and as enzyme inhibitors.

DETAILED DESCRIPTION OF THE PREFERRED EMBODIMENTS

The present invention is a hydrophilic ampholytic polymer or copolymer formed by copolymerization of:

a) 0.05 to 20 mole percent of at least one anionic monomer having at least one carboxy-functional group, b) 10 to 45 mole percent of at least one cationic monomer having at least one amino-functional group, c) a sufficient quantity (in an amount of about 35 to about 95 mole percent) of at least one non-ionic hydrophilic monomer to provide a glass transition temperature of above about 50° C., d) 0 to 10 mole percent of a fourth hydrophobic monomer, and e) 0 to 1.5 mole percent of a cross-linking monomer.

A variety of conventional polymerization techniques can be used to prepare the polymer, such as for example, solution, suspension, dispersion, or emulsion polymerization. A preferred method of preparation is by precipitation or inverse suspension polymerization of the polymer from a polymerization media in which the monomers are dispersed in a suitable solvent. When the copolymer has a $T_g$ of greater than 50° C., it can be precipitated from the polymerization media as a non-coalescing fine powder.

The monomers employed in preparing the copolymer are preferably water soluble and sufficiently soluble in the polymerization media to form a homogeneous solution. They readily undergo polymerization to form polymers which are water-dispersible or water-soluble.

Anionic monomers useful in forming the copolymer have at least one carboxy-functional group, such as an ethylenically unsaturated carboxylic acid having the structure which follows:

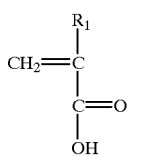
(A)

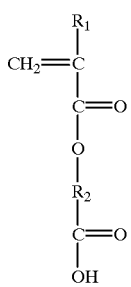
(B)

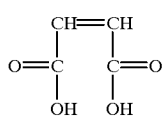
(C)

where
  $R_1$=—H, —$CH_3$, —$CH_2CH_3$, and
  $R_2$=—($CH_2$—)$_n$, where n=1 to 40, linear or branched alkyl, cycloalkyl, aryl, a polyethylene oxide chain having the formula —($CH_2$—$CH_2$—O—)$_p$ where p=1 to 50, or a polypropylene oxide chain having the formula —($CH_2(CH_3)$—$CH_2$—O—)$_p$ where p=1 to 100.

Examples of ethylenically unsaturated carboxylic acids include acrylic acid, methacrylic acid, itaconic acid, fumaric acid, maleic acid, and sulfoalkyl esters of unsaturated carboxylic acids, such as 2-sulfoethyl methacrylate, alone or in combination. Particularly preferred anionic monomers are methacrylic acid and acrylic acid.

Cationic monomers useful in forming the copolymer include at least one amino-functional group. In the copolymer, the amino groups ionize in the presence of an acid and thicken. The cationic monomer can be one having the following structures:

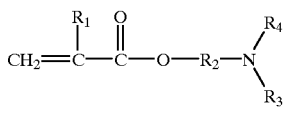
(A)

or

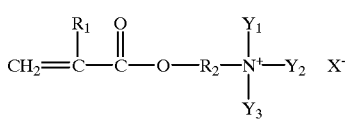
(B)

where
  $R_1$=—H, —$CH_3$, or —$CH_2CH_3$,
  $R_2$=—[$CH_2$—]$_n$, where n=1 to 40, linear or branched alkyl, cycloalkyl, aryl, a polyethylene oxide chain having the formula —($CH_2$—$CH_2$—O—)$_p$ where p=1 to 50, or a polypropylene oxide chain having the formula —($CH_2(CH_3)$—$CH_2$—O—)$_p$ where p=1 to 50, $R_3$, $R_4$, $Y_1$, $Y_2$, and $Y_3$ may be —H, —$CH_3$, —$CH_2$—$CH_3$, branched or linear alkyl, aryl, cycloalkyl, or combinations thereof.

Examples of cationic monomers include the following:

1) acrylamides, methacrylamides, vinyl amines, diallyl amines, vinyl heterocyclic amides, and combinations thereof, including N-(dimethylaminobutyl)acrylamide, N-(dimethylaminobutyl) methacrylamide, N-(dimethylaminopropyl)acrylamide, N-(dimethylaminopropyl) methacrylamide, N-(dimethylaminoethyl) methacrylamide, N-(dimethylaminoethyl) acrylamide; N-(dimethylaminomethyl)acrylamide, N-(dimethylaminomethyl)methacrylamide, N-(diethylaminopropyl)acrylamide, N-(diethylaminopropyl) methacrylamide, N-(dimethylaminoethyl) methacrylamide, N-(diethylaminoethyl)acrylamide, with N-(dimethylaminopropyl) methacrylamide being preferred.

2) acrylates and methacrylates selected such as N-(dimethylaminomethyl) acrylate, N-(dimethylaminomethyl) methacrylate, N-(dimethylaminopropyl) acrylate, N-(dimethylaminopropyl) methacrylate, N-(dimethylaminomethyl) acrylate, N-(dimethylaminoethyl) methacrylate, N-(dimethylaminoethyl)acrylate, N-(diethylaminoethyl) acrylate, N-(diethylaminoethyl) methacrylate, N-(2-methacryloyloxyethyl) ethylene urea, N-(diethylaminoethyl) methacrylate, N-(dimethylaminopropyl) methacrylate, and their chloride, sulfate, and sulfonate salts, as well as vinyl amines, such as vinyl pyridine and vinyl morpholine, diallyl amines, and their sulfate, sulfonate and chloride salts, dimethylaminoethyl methacrylate and their chloride and sulfonate salts being preferred;

3) chloride, sulfate, and sulfonate salts of N-(dimethylaminopropyl) acrylate, N-(dimethylaminobutyl) methacrylate, N-(dimethylaminobutyl) acrylate, N-(dimethylaminopropyl) methacrylate, N-(dimethylaminoethyl) methacrylate, N-(dimethylaminoethyl) acrylate, N-(diethylaminoethyl) methacrylate, N-(dimethylaminopropyl) methacrylamide;

4) aromatic and aliphatic vinyl or allyl amines selected from the group consisting of vinyl amine, vinyl piridine, vinyl morpholine, vinyl imidazole, dimethyl aminomethyl styrene, dimethyl aminoethyl styrene and their chloride, bromide, sulfate, sulfonate, phosphate, methyl and ethyl sulfonate salts;

5) diallyl amines having the following structure:

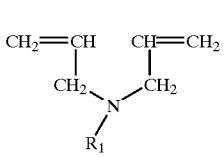
(A)

-continued

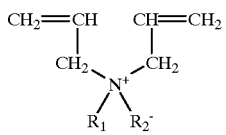
(B)

where $R_1$ may be: —H, —$CH_3$, —$CH_2$—$CH_3$, branched or linear alkyl, aryl, cycloalkyl, or combinations thereof.

$R_2$ is an acid radical such as chloride, bromide, sulfate, sulfonate, phosphate, methyl or ethyl sulfonate; and
6) combinations thereof.

While the cationic and anionic monomers have been described as separate monomers, it should be understood that a single monomer, having both an amino-functional and a carboxy-functional group could be substituted for the two types of monomers.

For ease of separation from a solvent media, the monomers are selected such that the resultant copolymer has a $T_g$ of greater than about 50° C. This allows the copolymer to be isolated in the form of a powder by precipitation from the reaction mixture. However, a number of low $T_g$ monomers can also be used in relatively small quantities without compromising the formation of the copolymers.

The non-ionic hydrophilic monomers are selected to impart water solubility to the resultant polymer and preferably are those that usually will enable achieving a high $T_g$ in the resultant copolymer Exemplary non-ionic monomers include ethylenically unsaturated amides having the following structure:

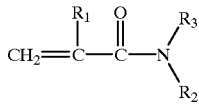

where $R_1$ is —H, —$CH_3$ or —$CH_2CH_3$, and
where $R_3$ and $R_2$ are selected from the group consisting of H, OH, methyl, ethyl, lauryl, stearyl, carboxy, and amino groups, and combinations thereof. In particular, the monomers consisting of acrylamide, methacrylamide, methyl acrylamide, dimethyl acrylamide, fumaramide, diacetone acrylamide, and dimethyl methacrylamide are preferred.

Other examples include fumaramide; N-vinyl pyrrolidone; hydroxyethyl methacrylate (HEMA); hydroxyethyl acrylate (HEA); hydroxypropyl acrylate; methylol acrylamide; hydroxypropyl methacrylate. Other suitable non-ionic hydrophilic monomers belong to the family of methoxy-polyethylene-oxide, acrylates, methacrylates and can be represented by the following structure:

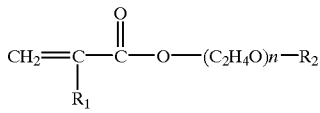

where $R_1$ is —H, —$CH_3$, or —$CH_2CH_3$, and
where $R_2$ is H, OH, methyl, ethyl, lauryl, stearyl, carboxy or an amino group, alone or combinations thereof and n=1 to 100. Monomers of the type represented in the structure tend to lower the $T_g$ of the copolymer. Consequently, they are preferably added in relatively small amounts.

Other non-ionic hydrophilic monomers can be cyclic amides having the following structure:

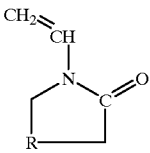

where R is an alkylene group such as —$[CH_2—]_n$, n=1 to 4, such as vinyl pyrrolidone (n=1), vinyl caproclactam (n=2), or any combination of non-ionic monomer can be used.

Particularly preferred hydrophilic monomers are hydroxyethyl methacrylate, hydroxyethyl acrylate, methacrylamide, vinyl pyrrolidone, and hydroxypropyl methacrylate.

Table 1 lists the glass transition temperatures $T_g$ of homopolymers formed from selected monomers suitable for incorporation in the copolymer of the present invention.

TABLE 1

| MONOMERS | $T_g$° C. |
|---|---|
| N-Vinyl Pyrrolidone (NVP) | 120 |
| Acrylic Acid (AA) | 100 |
| Methacrylic Acid (MAA) | 180 |
| Hydroxyethyl Methacrylate (HEMA) | 80 |
| Methacrylic Acid (MAA) | 185 |
| Diacetone Acrylamide (DAAAm) | >80 |
| Dimethyl Acrylamide (DMAAm) | >80 |
| Acrylamide (AAm) | >100 |
| Aceto Acetoxy Ethyl Aceto Acetate (AAEAA) | >60 |
| Dimethyl Aminopropyl Methacrylamide (DMAPMA) | 96 |

Optionally, a hydrophobic monomer is employed to modify the properties of the resulting copolymer. Suitable hydrophobic monomers include those which are (1) water-insoluble, (i.e., less than 0.2 weight part of the hydrophobic monomer will dissolve in 100 weight parts of water) and (2) ethylenically unsaturated compounds having hydrophobic associative groups, herein referred to as hydrophobic moieties usually added at less than 2% mol of the total copolymer composition. The hydrophobic monomer increases the thickening efficiency of the copolymer through inter molecular, non-polar association.

The hydrophobic moieties preferably have at least 4 carbon atoms and are most preferably pendant organic groups having hydrophobic character comparable to one of the following: aliphatic hydrocarbon groups having at least four carbons such as $C_4$ to $C_{20}$ alkyls and cycloalkyls; polynuclear aromatic hydrocarbon groups such as napthyls; alkylaryls, wherein the alkyl has one or more carbons, preferably 4 to 8 carbons; haloalkyls of 4 or more carbons, preferably perfluoroalkyls; polyalkyleneoxy groups wherein the alkylene is ethylene, propylene or a higher alkylene and there is at least 1 alkyleneoxy unit per hydrophobic moiety. The hydrophobic monomers are represented by the following formulas:

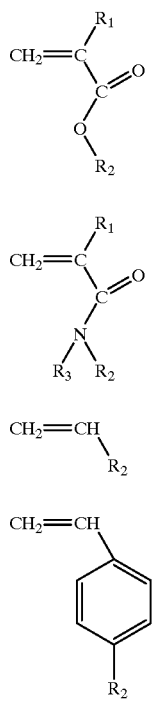

(A)

(B)

(C)

(D)

where
- $R_1$ is selected from hydrogen, methyl and ethyl groups,
- $R_2$ and $R_3$ is selected from alkyl groups having from 1 to 30 carbon atoms. They can be linear or branched,
- $R_2$ and $R_3$ can also be selected from hydrogen or methoxy terminated oxyethylene and oxypropylene groups with structure:

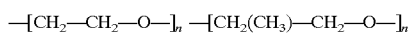

where n is an integer from 1 to 100.

Exemplary hydrophobic monomers include the higher alkyl esters of α, β-ethylenically unsaturated carboxylic acids, such as dodecyl acrylate, dodecyl methacrylate, tridecyl acrylate, tridecyl methacrylate, tetradecyl acrylate, tetradecyl methacrylate, octadecyl acrylate, octadecyl methacrylate; ethyl half esters of maleic anhydride, diethyl maleate; and other alkyl esters derived from the reactions of alkanols having from 4 to 20, preferably from 8 to 20, carbon atoms with ethylenically unsaturated carboxylic acids, such as acrylic acid, methacrylic acid, maleic anhydride, fumaric acid, itaconic acid and aconitic acid; alkylaryl esters of ethylenically unsaturated carboxylic acids such as nonyl-∀-phenyl acrylate, nonyl-∀-phenyl methacrylate, dodecyl-∀-phenyl acrylate and dodecyl-∀-phenyl methacrylate; N-alkyl, ethylenically unsaturated amides such as N-octadecyl acrylamide; N-octadecyl methacrylamide, N,N-dioctyl acrylamide and similar derivatives thereof; ∀-olefins, such as octene-1, decene-1, dodecene-1, and hexadecene-1; vinyl alkylates wherein the alkyl has at least 8 carbons, such as vinyl laurate and vinyl stearate; vinyl alkyl ethers, such as dodecyl vinyl ether and hexadecyl vinyl ether; N-vinyl amides such as N-vinyl lauramide and N-vinyl stearamide; and ar-alkylstyrenes such as t-butyl styrene.

Of the foregoing, the preferred hydrophobic monomers are the alkyl esters of acrylic acid, methacrylic acid, N-alkyl acrylamides and N-alkyl methacrylamides, wherein the alkyl has from 8 to 20 carbon atoms, and the alkyl styrenes, wherein the alkyl has from 4 to 8 carbons. The alkyl methacrylates, wherein the alkyl has from 10 to 20 carbon atoms. Dodecyl methacrylate and N-dodecyl methacrylamide are the most preferred hydrophobic monomers. One or more hydrophobic monomers may be used, depending on the desired properties of the copolymer.

With regard to the polymerization solvent of choice for use in the polymerization process, the solubility parameter of the solvent is preferably close to that of the selected monomers. The solubility parameter has been defined as the square root of the cohesive energy density which represents the concentration of forces which cause molecules to cohere. If the solubility parameter of the solvent is much higher than that of one of the monomers, either the monomer does not dissolve readily in the solvent, or the resulting copolymer has a tendency to precipitate too quickly, and its effectiveness as a thickener is reduced. If the solubility parameter of one of the monomers is substantially higher than that of the solvent, the resulting copolymer has a tendency to swell. As a result, mixing of the polymerization media becomes difficult. Preferably, the solubility parameters of the monomers are no more than 2 $(MPa)^{1/2}$ below that of the solvent. Table 2 lists a number of monomers and solvents and their corresponding solubility parameters.

TABLE 2

| | SMALL'S SOLUBILITY PARAMETER $(MPa)^{1/2}$ |
|---|---|
| MONOMERS | |
| N-Vinyl Pyrrolidone (NVP) | 17.0 |
| Methyl Methacrylate (MMA) | 18.09 |
| Acrylic Acid (AA) | 21.96 |
| Ethyl Methacrylate (EMA) | 17.75 |
| Hydroxyethyl Methacrylate (HEMA) | 20.60 |
| Methacrylic Acid (MAA) | 20.43 |
| Hydroxyethyl Acrylate (HEA) | 19.11 |
| Diacetone Acrylamide (DAAAm) | 22.09 |
| Dimethyl Acrylamide (DMAAm) | 20.39 |
| MethAcrylamide | NA |
| Acrylamide (AAm) | 21.24 |
| Dimethyl Amino Ethyl Methacrylate (DMAEMA) | 15.97 |
| Aceto Acetoxy Ethyl Aceto Acetate (AAEAA) | 19.69 |
| Methoxy-(EO9)-Methacrylate (CD 550) | 18.84 |
| Methoxy-(EO12)-Methacrylate (CD 552) | 17.25 |
| Dimethyl Aminopropyl Methacrylamide (DMAPMA) | 19.94 |
| SOLVENTS | |
| Cyclohexane | 15.5 |
| Ethyl Acetate | 18.22 |
| Ethanol | 24.77 |
| n-Butyl Acetate | 17.65 |
| t-Butyl Acetate | 16.20 |
| Methyl Acetate | 18.97 |
| Benzene | 18.8 |
| Methylene Chloride | 19.8 |
| t-butyl Alcohol | 21.7 |

As can be seen from Table 2, the preferred solvent varies with the choice of monomers. For example, monomers such as n-vinyl pyrrolidone (NVP), hydroxyethyl methacrylate (HEMA), dimethyl aminopropyl methacrylamide (DMAPMA), Methyl Methacrylate (MAA), and Acrylic Acid (AA) are compatible with cyclohexane, ethyl acetate, and butyl acetate solvents. HEA, CD 550, and CD 552 polymerize well in ethyl acetate.

The selected solvent may be a blend of two or more solvents. This allows the solubility parameter range to be adjusted so that the solvent is compatible with the chosen monomers. One preferred blend of solvents is a blend of a hydrocarbon, such as cyclohexane, with an alkyl acetate ester, such as ethyl acetate. Particularly preferred solvents have a boiling point of below 100° C. so that they can be removed from the copolymer by evaporation under moderate temperature and pressure conditions.

Examples of suitable polymerization solvents are aliphatic hydrocarbons, such as pentane, hexane, heptane, cyclohexane; mineral spirits; mineral oils; branched hydrocarbons, such as those distributed by Presperse, Piscataway, N.J., under the trade name of Permethyl 97A to 106A; ethers, such as dimethyl ether and diethyl ether, esters, such as n-butyl acetate, t-butyl acetate, propyl acetate, ethyl acetate, and methyl acetate; aromatic hydrocarbons such as benzene, toluene, and xylene; perfluorinated fluids, such as perfluorohexane, perfluorooctane, perfluoroalkyl ether, perfluoroalkyl amines, and trifluoro ethanol; alcohols, such as t-butyl alcohol, isopropyl alcohol, and methanol; and halogenated solvents such as methylene chloride. The solvents may be used alone or in combination.

A cross-linking monomer, or crosslinker is added to the polymerization media to modify and control the properties achieved by the resulting copolymer. This would give a formulation, thickened with the polymer of the present invention, an aesthetically desirable appearance and rheology and allow portions of the product to be dispensed as required. For example, a hair gel or toothpaste will flow out of a squeezable tube for application, while the remaining product pulls back to remain with the package after release of the pressure.

The cross-linking monomer employed is represented by the formula:

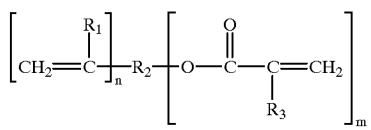

n, m=1 to 4, n+m≧2

$R_1$, $R_3$=H, alkyl $R_2$=alkyl, cycloalkyl, aryl,
=—($CH_2$—$CH_2$—O)$_p$— where p=1 to 50,
=—($CH_2(CH_3)$—$CH_2$—O)$_p$— where p=1 to 50,
=amido, ester, polyamido, polyester Suitable cross-linking monomers include di-, tri- or polyfunctional monomers of vinyl, allyl, acrylic or methacrylic, acrylamido or methacrylamido.

Examples include triallyl-1,3,5-triazine-2,4,6(1H,3H, 5H)-trione, ethylene glycol diacrylate, triacrylate, trimethylol propane trimethacrylate, allyl methacrylate, allyl citrate, di- and tri-allyl amine, polyethylene glycol di- and tri-acrylates, allyl pentaerythritol, allyl sucrose, and methylenebisacrylamide. Particularly preferred cross-linking monomers are ethylene glycol dimethacrylate, trimethylol propane trimethacrylate, allyl pentaerythritol, and triallyl-1,3,5-triazine-2,4,6(1H,3H,5H)-trione.

Optionally, the hydrophilic ampholytic polymer of the present invention can be a linear un-cross-like linked polymer. Such polymers would be useful for scale inhibition, dispersant applications, and general purpose viscosity modification, especially in the presence of cationic materials.

An initiator is used to catalyze the polymerization reaction. Any conventional free radical initiator can be used, including azo- and peroxo-type initiators. Examples of suitable azo-type initiators are azobis-dimethylvaleronitrile, azobis-isobutyronitrile, azobis-methylbutyronitrile and other azo-initiators sold by DuPont, under the trade name VAZO®, and by WAKO Pure Chemical Industries, under the trade names of V-40 to V501.

Examples of suitable peroxo-type initiators include lauryl peroxide, cumene hydroperoxide, ethyl hexyl peroxodicarbonate, diisopropyl peroxydicarbonate, 4-(t-butylperoxylperoxycarbonyl)-3 -hexyl-6-7-(t-butyl-peroxycarbonyl)heptyl cyclohexene (4-TBPCH), cumene hydroperoxide and t-butyl peroxyneodecanoate, t-butyl hydroperoxide, benzoyl peroxide, and other organic peroxides sold by Elf Atochem North America, Inc., under the trade names of Lupersol®, Luperco®, Lucidol®, and Luperox®.

In particular, a preferred initiator is 2,2'-azobis(2-methylbutyronitrile), sold by DuPont under the trade name VAZO® 52. Other methods suitable for the polymerization of ethylenically unsaturated monomers such as cationic, anionic or redox-pair initiators can also be used to prepare the ampholytic polymers of this invention.

The monomers, cross-linking monomer, and initiator are preferably combined in the polymerization media in the following proportions:

| | |
|---|---|
| anionic monomers | 0.05–20 mole percent |
| cationic monomers | 10–45 mole percent |
| non-ionic hydrophilic monomers | 45–90 mole percent |
| hydrophobic monomers | 0–10 mole percent |
| cross-linking monomer | 0.005–1.5 mole percent |
| initiator | 0.005–1 mole percent |

Particularly preferred ranges of monomers are:

| | |
|---|---|
| anionic monomers | 0.05–10 mole percent |
| cationic monomers | 20–35 mole percent |
| non-ionic hydrophilic monomers | 55–75 mole percent |

The preferred ratio of monomer is determined by the percent mole ratio of cationic to anionic monomer as follows:

Ratio (R)=Cationic Monomer÷Anionic Monomer

A preferred ratio of cationic monomers to anionic monomers is from about 2 to about 16, with the ratio of about 3 to 16 being further preferred. Selecting a ratio within this range has two advantages. First, it facilitates polymerization. The cationic and anionic monomers form inter and intra salt units which cause the copolymer to precipitate from the solvent in the form of a fine powder. This facilitates formation of the copolymer by precipitation polymerization. Second, the presence of anionic and cationic groups in the same polymeric molecule renders the copolymer compatible with cationic, anionic, and amphoteric surfactants typically used in cosmetic, household, cleaning, pharmaceutical, and other formulations.

The preferred ratio of monomers to solvent, i.e., the total solids, is from about 10 to about 30% by weight of the contents of the reactor. At about 30% by weight, or above, the reaction is difficult because reactants tend to form gels or solidify as a compacted mass inside the reactor, making processing of the copolymer difficult, unless some means for reducing the viscosity or facilitating the reaction is employed.

Other polymerization additives, such as non-ionic surfactants, polymeric stabilizers, dispersing agents, acids, bases, and salts, can be used, either during or post polymerization. Such polymerization additives are used to facilitate polymerization by preventing agglomeration of the polymer particles as they are formed in the reactor.

Suitable nonionic surfactants for this purpose are added at from about 0.01% wt to 4% wt of the total mass in the reactor and include those with a hydrophobic/hydrophilic balance (HLB) of from about 2 to 16. Most preferred are those with an HLB of 2 to 8. Exemplary surfactants include alkyl polyethyleneoxy compounds represented by the formula:

$$RO(EO)_n-H,$$

wherein R is a $C_8$ to $C_{18}$ alkyl, EO is ethyleneoxy and n is an integer from 1 to 10. Of the foregoing surfactants, the ethoxylated alkyl phenol and ethoxylated fatty alcohols are more preferred. Other suitable nonionic surfactants include those described in McCutcheon's, Detergents and Emulsifiers, North American Edition, 1980 Annual, ones sold by ICI Co. under the trade name, Hypermer polymeric surfactants or dispersants, and glycols and dimethicone copolyols, most broadly known as polysiloxane polyether copolymers, represented by the formula:

$$(CH_3)SiO(CH_3)SiO)_x(CH_3 \underset{|}{SiO})_y Si(CH_3)_3$$
$$PE$$

where
  x=2–200;
  y=2–100;
  PE=$(CH_2)_p O(EO)_m (PO)_n Z$, alkyl radical, $(Me_2SiO)_p Z$
    where EO=—$CH_2CH_2O$—, ethyleneoxy;
    PO=—$CH_2CH(CH_3)O$, 1,2-propyleneoxy;
    p=2–30;
    m=0–100;
    n=0–100; and
    Z=alkyl radical.

A number of polymers of this type are available from Witco Co. under the trade name of Silwet, from Dow Corning under the trade names, DC or DC Surfactant, and from Goldshmidt Co. under the trade name, Abil surfactants.

To prepare the copolymers of the present invention, the selected monomers, crosslinker, solvent, and surfactant are mixed to form a homogenized solution. The mixture is blanketed with an inert gas, such as nitrogen, and heated to about 30–90° C., more preferably, about 40–60° C. A first portion of initiator, or batch initiator, is added and the reactants stirred for a period sufficient for polymerization, typically about 5 hours. A second portion of initiator, or "kick" initiator, is added when polymerization is essentially complete. This reduces the concentration of any residual monomers by copolymerizing them. The "kick" initiator may be the same as the batch initiator, or a different initiator.

Alternatively, one or more of the monomers is added incrementally, with a portion of the monomer being added following the addition of the initiator.

During the reaction, the copolymer precipitates from the solvent as a fine powder. This forms a slurry with the solvent. The solvent is removed, for example by rotary evaporation. The copolymer product may be further dried to complete solvent removal. The copolymer remains as a powder or friable solid.

The copolymers formed are effective rheology modifiers and thickeners for a wide variety aqueous formulations, including organic acid formulations, inorganic acid formulations, hair conditioners, shampoos, fabric softeners, and the like, pharmaceutical, personal care and household formulations. The formulations show good retention of viscosity over a wide range of pH and in the presence of cationic surfactants.

The copolymer is compatible with a variety of hair conditioning agents, including silicone conditioning agents, cationic surfactant conditioning agents, amphoteric surfactants, and other conditioning agents found in hair care compositions and personal care products.

Examples of compatible silicone conditioning agents include volatile silicones, such as cyclic or linear polydimethyl siloxanes of the general formula:

$$(CH_3)_3Si-O-[-Si(CH_3)_2-O-]_n-Si(CH_3)_3$$

where n is an integer from 1–7.

The copolymer is also compatible with non-volatile silicone conditioning agents, such as polydimethylsiloxane gums, aminosilicones and phenyl silicones, such as polyalkyl or polyaryl siloxanes. Particularly preferred silicones of this type are polydimethyl siloxane, polydiethyl siloxane, and polymethylphenylsiloxane.

Other silicone cationic polymers which are compatible with the copolymer correspond to the formula:

$$(R_1)_a G_{3a}-Si-(-OSiG_2)_n-(-OSiG_b(R_1)_{2b})_m-O-SiG_{3a}(R_1),$$

where G is selected from the group consisting of hydrogen, phenyl, OH, $C_1$–$C_8$ alkyl groups, preferably methyl, and where a denotes 0 or an integer from 1 to 3, and preferably equals 0; b denotes 0 or 1, and preferably equals 1; the sum n+m is a number from 1 to 2,000, and preferably from 50–150, n denoting an integer from 0 to 1,999, and preferably from 49–149, and m denoting an integer from 1 to 2000, and preferably from 1 to 10; $R_1$ is a monovalent radical of the general formula $C_qH_{2q}L$, where q is an integer from 2 to 8 and L is selected from the groups —$N(R_2)$ $CH_2$—$CH_2$—$N(R_2)_2$ and —$N(R_2)_2$, where $R_2$ is selected from the group consisting of hydrogen, phenyl, benzyl, and saturated hydrocarbon radicals, preferably alkyl radicals containing from 1 to 20 carbon atoms.

Rigid silicone polymers are also compatible with the present copolymer. These include polydimethyl siloxane gums and polyphenyl methyl siloxane gums, commonly known as dimethicone, amodimethicone, phenylmethicone. Examples include filler reinforced polydimethyl siloxane gums, such as those having end groups such as hydroxyl; cross-linked siloxanes, such as organic substituted silicone elastomers; organic substituted siloxane gums, including those having end groups such as hydroxyl; resin reinforced siloxanes; and cross-linked siloxane polymers. One such siloxane gum is a diphenyl-dimethyl polysiloxane gum having a molecular weight of at least about 500,000 and which is diphenyl-substituted.

Silicone resins compatible with the copolymer are silicone polymers with a high degree of cross linking introduced through the use of trifunctional and tetrafunctional silanes. Typical silanes used in the manufacture of such resins include monomethyl, dimethyl, monophenyl, diphenyl, methylphenyl, monovinyl, and methylvinyl chlorosilanes, and tetrachlorosilane. Other functional silicone materials include silicone glycol copolymers, such as those sold by Dow Corning Corp., Midland, Mich., under the trade names DC 190 and DC 193.

Cationic surfactant conditioning agents compatible with the copolymer include quaternary ammonium salts, such as dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominantly from 16 to 18 carbon atoms). Examples of such quaternary ammonium salts include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride, cetyl trimethyl ammonium chloride, and behenyl trimethyl ammonium chloride are preferred quaternary ammonium salts useful herein. Di-(hydrogenated tallow) dimethyl ammonium chloride is a particularly preferred water-insoluble quaternary ammonium salt for use as a conditioning agent in hair care compositions which is also compatible with the present copolymer.

Salts of primary, secondary, and tertiary fatty amines are also preferred water-insoluble cationic surfactant materials for use as hair conditioning agents which are compatible with the present copolymer. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tridecyl amine, ethyl stearylamine, ethoxylated (2 moles ethylene oxide) stearylamine, dihydroxyethyl stearylamine, and arachidylbehenylamine. Suitable amine salts include the halogen, acetate, phosphate, nitrate, citrate, lactate, and alkyl sulfate salts. Such salts include stearylamine hydrochloride, soyamine chloride, stearylamine forrnate, N-tallowpropane diamine dichloride, stearamidopropyl dimethylamine citrate, stearamido propyldimethyl amine, and guar hydroxypropyl triammonium chloride.

Amphoteric surfactants compatible with the present copolymer include high alkyl betaines, sulfo betaines, amido betaines, and amidosulfobetaines, such as cetyl betaine, and derivatives of aliphatic secondary and tertiary amines in which the aliphatic radical can be straight chain or branched and wherein one of the aliphatic substituents contains from about 8 to about 18 carbon atoms and one contains an anionic water solubilizing group, such as carboxy, sulfonate, sulfate, phosphate, or phosphonate. Examples of compounds falling within this definition are sodium 3-dodecylaminopropionate, N-alkyltaurines such as the one prepared by reacting dodecylamine with sodium isethionate, and N-higher alkyl aspartic acids. Others include alkyl, preferably $C_6$–$C_{22}$ and most preferably $C_8$–$C_{12}$, amphoglycinates; alkyl, preferably $C_6$–$C_{22}$ and most preferably $C_8$–$C_{12}$, amphopropionates; and mixtures thereof.

Suitable zwitterionic surfactants for use in hair care compositions and which are compatible with the present copolymer are exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as a carboxy, sulfonate, sulfate, phosphate, or phosphonate group. Examples include alkyl amino sulfonates, alkyl betaines, and alkyl amido betaines.

Additional hair conditioning agents are used in hair care compositions to provide enhanced conditioning benefits, and which are also compatible with the present copolymer, are hydrolyzed animal and vegetable protein conditioning agents.

A common component in the preparations of cleaning compositions such as shampoo, hair conditioning, industrial and household cleaners, and detergent compositions is a synthetic anionic surfactant. The surfactants are present at a level of from about 5% to about 25%, preferably from about 15% to about 20% and are compatible with the polymers of the present invention. These synthetic anionic surfactants include alkyl and alkyl ether sulfates, represented by the formulae $ROSO_3$ M and $RO(C_2 H_4O)_x SO_3$ M wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols are those derived from coconut oil. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates for use with the present invention are sodium coconut alkyl trioxyethylene sulfate; lithium tallow alkyl trioxyethylene sulfate; and sodium tallow alkyl hexaoxyethylene sultate. Highly preferred alkyl ether sulphates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another class of anionic surfactants, which are compatible with the polymers of the present invention, are the water-soluble salts of the organic, sulfonic acid reaction products of the general formula:

$$RSO_3 \text{ M}$$

wherein R is chosen from the group consisting of a straight or branched chain, saturated aliphatic hydrocarbon radical having from 8 to 24, preferably 12 to 18, carbon atoms; and M is a cation. Examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis, such as alkali metal and ammonium sulfonated $C_{12-18}$ n-paraffins.

Additional examples of anionic synthetic detergents which are compatible with the polymers of the present invention are the following:

a) the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil, b) succinamates, which includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid, c) olefin sulfonates having about 12 to about 24 carbon atoms, which includes compounds which can be produced by the sulfonation of alpha-olefins by means of uncomplexed sulfur trioxide, followed by neutralization of the acid reaction mixture in conditions such that any sultones which have been formed in the reaction are hydrolyzed to give the corresponding hydroxyalkanesulfonates. The sulfur trioxide can be liquid or gaseous, and is usually, but not necessarily, diluted by inert diluents, for example by liquid $SO_2$, chlorinated hydro-carbons, etc., when used in the liquid form, or by air, nitrogen, gaseous $SO_2$, etc., when used in the gaseous form. The alpha-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene, d) betaalkyloxy alkane sulfonates, such as beta-alkyloxyalkane-1-sulfonates, or alternatively 2-alkyloxyalkane-1-sulfonates, having low hardness (calcium ion) sensitivity useful herein to provide superior cleaning levels under household washing conditions include: potassium beta-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium beta-methoxyoctadecylsulfonate, and ammonium-n-propoxydodecylsulfonate, and e) other synthetic anionic surfactants such as those that are described in McCutcheon's, Detergents and Emulsifiers, 1994, published by M.C. Publishing Corporation, which is incorporated herein by reference and in U.S. Pat. No. 3,929,678, Dec. 30, 1975 to Laughlin et al. The above-mentioned surfactants can be used alone or in combination in the shampoo compositions of the present invention. Mixtures of alkyl sulfates and ethoxylated alkyl sulfates are preferred for use herein.

Additionally, in many types of formulation compositions, the detergent system can be prepared by using non-ionic surfactants blends. The surfactant is present at a level of from about 5% to about 25%, preferably from about 15% to about 20%. Suitable detergent systems are composed of nonionic surfactants with hydrophobic/hydrophilic balance, HLB, from about 2 to 16. Most preferred are those with HLB=8–18. Examples of these surfactant include alkyl polyethyleneoxy compounds represented by the formula, $RO(EO)_n$—H, wherein R is $C_8$–$C_{18}$ alkyl, or phenyl. EO is ethyleneoxy and n is a number from 1 to 100. Other suitable nonionic surfactants are described in McCutcheon's, Detergents and Emulsifiers, 1994, M.C. Publishing Corporation. Of the foregoing surfactants, the ethoxylated alkyl phenol and ethoxylated fatty alcohols are more preferred. Alkanolamides such as Cocamide MEA, Cocamide DEA, and Lauramide DEA are just a few examples of the alkanolamides that may be used. Amine oxides such as cocamidopropylamine oxide stearamine oxide, lauramine oxide, and behenamine oxide.

To modify rheology and/or thicken a selected composition, the copolymer is added to the composition as a fine powder at a concentration of from about 0.01% wt. to 20% wt. and the mixture stirred. Heat may be applied to aid dispersability or dissolution of the copolymer. The copolymer is neutralized with an inorganic, organic, or amino acid to bring about the thickening process. The amount of acid required depends on the viscosity and pH of the desired formulation. Suitable acids for neutralization include, but not limited to, acetic, hydrochloric, hydrofluoric, hydroiodic, hydrobromic, nitric, phosphoric, sulfuric, polyacrylic, formic, glycolic, lactic, malic, citric, mandelic, and tartaric acids, carboxylic acids of the general formula $R_nCOOH$, where n is an integer from 1 to 18, and amino acids in general.

The ampholytic copolymer is also suitable for the preparation of shampoos, conditioners, rinses, liquid soap, soap bars, detergents, cleaners, room deodorizers, and the like.

In general, the polymers of this invention can be used in a host of applications where the presence of acidic and basic groups in the same molecule is a useful property. They can be used as additives in cosmetic applications, body implants, coatings for catheters, cannulae, antiperspirant and deodorant formulations, coating for medical devices, gloves, removable protective coatings, wound dressings, etc. They can be used in the formulation of inks, protective washable coatings for textiles, etc. They can be used to thicken organic or inorganic acid systems.

The copolymer is suitable for use as thickening and/or conditioning additive in the formulation of hair creams, skin creams, lotions, pomades, and ointments, topical medicated creams, skin protective films, hair depilatories, hair shaving creams, hand and body lotions, mascaras, sunscreens, and the like.

The copolymer also finds application as an additive in nail care formulations, such as water-based nail polish, nail repair, nail protection, and the like.

In cosmetic applications, the copolymer can be used as a wet & dry conditioner, rinse out conditioner, in conditioning shampoo, conditioning styling gel, 2 in 1 conditioning body wash, conditioning/post treatment (color enhancing resins) of hair color, moisturizing body wash, skin moisturizer, protective cream, antiperspirants, alpha hydroxy acid (AHA) containing formulations, self tanning applications with dihydroxyacetone (DHA), skin whitening formulations containing kojic acid, natural extracts and hydroquinone.

The resultant copolymers can be used in home care or in fabric softener, disinfectant cleaner, bath room cleaners, toilet bowls, hand soaps, disinfectant, and alkali strippable vinyl floor polish formulations.

Another use is in formulating for medical applications as hand creams, antiviral (anionic viruses), antibiotic, gastric bio-adhesive, super-absorber in diaper applications, ion exchange, non drip sprayable disinfectant in hospitals, hard surface antimicrobial finish applied during routine maintenance, control release of drugs in stomach (low pH from tablets).

A further use is textile, inks and paper applications as flocculent for phenolics (paper mill effluent), paper coatings, antiwicking for ink jet inks, thickener for ink formulations such as cationic dyes for use in printing acrylic fabrics, binder for paper (anionic pulp), saturating non woven fabrics to obtain synthetic leathers, and protective washable coatings for textiles.

The polymer also finds utility in general industrial applications such as deck and fence wash, anti-freeze, shear thinning deicers, pickup acid and alkali spills, in water treatment, as crosslinkers for epoxy's, as cement plasticizer, to stabilize asphalt emulsions at low pH, to make clear adhesives, as dispersion stabilizer of clay, titanium dioxide, calcium carbonate and other minerals, pickling agents in cold rolled steel process, industrial metal coatings at low pH, extracting microbes from aqueous systems, leather processing aid (bonds with the carboxylated proteins).

The copolymer can also be used in the formulation of pharmaceutical formulations, such as creams, pomades, gels, tooth paste, tablets, gel capsules, enema fluids, vomitives, suppositories, foamed anti-fungal preparations. The copolymer can be used as a vehicle in topical and systemic drug delivery compositions, compositions to deliver transdermally active ingredients to or through the skin, ocular fluids, anti-acne formulations, topical analgesics, and the like.

The copolymer has a number of properties which suit it to a variety of medical and dental applications. First, the copolymer is able to act as a thickener for increasing the viscosity of liquid forms of therapeutic agents, such as syrups, gels, and the like. Second, the copolymer is compatible with cationic materials, and thus may be used in oral care and medical compositions where cationic agents are used. For example, oral care compositions for plaque and tartar control often contain biocides. These are often cationic in nature and thus many conventional thickeners are incompatible with the biocide. Further, the anionic characters of the ampholytic polymer would be beneficial in inhibiting calcium phosphate build up and in inhibiting the enzymatic hydrolysis of pyrophosphate, a commonly used tartar control agent. The present copolymer is compatible with a variety of both cationic and anionic materials and thus has applicability as a thickener and carrier in such compositions. Thus, they can be used in various applications such as body implants, coatings for catheters, cannulae, antiperspirant and deodorant formulations, coating for medical devices, gloves, removable protective coatings, wound dressings, and the like.

Third, the copolymer has bioadhesive properties. By selecting the relative proportions of cationic and anionic groups in the copolymer, the copolymer can be tailored such that it adheres preferentially in a particular region of the gastro-intestinal system depending on the local pH. The bioadhesive properties of the copolymer are effective in a variety of drug delivery systems, including tablets, pills, syrups, and the like. For example, when used in tablets, the copolymer assists the tablet in adhering to the membrane of the chosen site in the digestive system so that, as the pill swells, the drug is released in high concentration at the selected site of absorption.

Fourth, the copolymer has properties as an absorption or penetration enhancer. While not fully understood, it is believed that paracellular transport of drugs is facilitated by the copolymer. It is likely that the copolymer assists in opening the tight junction between epithelial cells so that the drug may pass therethrough.

Fifth, the copolymer is capable of acting as an ion binding agent. For example, the copolymer effectively binds phosphates in the blood stream over a wide range of pH. The copolymer may thus be used in the treatment of hyperphosphatemia.

Clearly, many applications can take advantage of two or more of the properties of the copolymer. For example, in the case of phosphate binding, the ability of the copolymer to act as an absorption enhancer allows the copolymer to be used in oral compositions.

In another embodiment, the copolymer is used in the oral delivery of insulin and other proteins and peptides to the blood stream from the gastrointestinal system. First, the copolymer is compatible with insulin and other proteins and peptides. The anionic portions of the copolymer act to keep the insulin in solution at low pH. Second, the bioadhesion properties of the copolymer act to concentrate the insulin adjacent to the membrane of the intestinal tract where it can transported into the blood stream. Third, the penetration enhancing characteristics of the copolymer facilitate this transport process. To protect the insulin from degradation in the stomach and intestinal tract by trypsin and chymotrypsin, compositions containing the copolymer and insulin preferably also include an enzyme inhibitor. Optionally, the enzyme inhibitor is chemically attached to the copolymer. As with other drug delivery systems, the insulin/copolymer system may be used in the form of tablets, pills, capsules, suspensions, syrups, and the like.

In general, therefore, the copolymers of this invention can be used in a host of applications where the presence of acidic and basic groups in the same molecule is a useful property.

While not intended to limit the invention, the following examples are illustrative of the methods of preparing the copolymers of the present invention, their properties, and formulations in which they can be used. Throughout, viscosities were measured using a Brookfield Viscometer with RV spindles. All viscosities were measured at 20 rpm.

EXAMPLES

General Example of Preparation of Hydrophilic Ampholytic Polymers

In a jacketed reactor provided with a condenser, turbine mixer and temperature probe, the monomers, crosslinker, surfactant, and solvent were mixed to homogenize. The mixture was heated to 60° C. and blanketed with nitrogen. In each example, the surfactant employed was Hypermer® B-246 surfactant (supplied by ICI Industries), except for Examples 12 and 13 where Abil EM90, a siloxane glycol surfactant (available from Goldschmidt, Richmond, Va.) was employed, although other surfactants could be used. A batch initiator, VAZO 52, sold by DuPont, was added to the reactor and the reactor stirred for 5 hrs. As is common for polymer reactions of this type, a kick initiator, or "kicker" in an amount of 0.012% by weight based upon the weight of the polymer was added after 5 hrs. of reaction to reduce the concentration of residual monomers. The preferred "kicker" is VAZO 52, although other initiators could be employed. The "kicker" does not materially alter the polymer composition which is the end product of the reaction. Further, a "kicker" will be employed to consume the residual monomers in the additional examples which follow, but this step is implied and not specifically discussed in the examples. The precise amount of initiator will vary with the reaction, usually in an amount of about 0.005 to 0.05% by weight, with enough initiator being employed to consume the monomers and produce a polymer with significantly reduced monomer residuals. In the present reaction, the reaction was stopped at 7 hrs. and the product removed from the reactor in the form of a paste.

The solvent was separated from the copolymer paste by drying in a rotary evaporator under a vacuum of 23 in. Hg at a temperature of 55° C. for 12 hours. The product was dried at 77° C. for a further 3 hours.

This procedure was used to prepare the polymers in Examples 1 to 37.

Example 1

Preparation of a HEMA/DMAPMA/MAA Polyampholyte in a Solvent Blend

| DMAPMA/MAA = 3.1% mol/mol | | |
|---|---|---|
| Reagent Name | % wt | % Mol |
| Methacrylic Acid (MAA) | | 9.662 |
| Dimethylaminopropyl Methacrylamide (DMAPMA) | | 30.000 |
| Hydroxyethyl Methacrylate (HEMA) | | 60.000 |
| Trimethylolpropane trimethacrylate | | 0.300 |
| VAZO 52 | | 0.038 |
| Total (Polymer) | | 100.0 |
| Total Solids = | 20.00 | |
| Surfactant | 0.674 | |
| Ethyl Acetate/Cyclohexane = 54/46% wt | 79.326 | |
| Total | 100.0 | |

The solvent used was a blend of two solvents, ethyl acetate and cyclohexane. The surfactant used is a nonionic block copolymer surfactant sold under the Hypermer trade name, by ICI Surfactants, Wilmington, Del.

Example 2

Preparation of a HEMA/DMAPMA/MAA Polyampholyte in a Solvent Blend

| DMAPMA/MAA = 6.43% mol/mol | | |
|---|---|---|
| Reagent Name | % wt | % Mol |
| Methacrylic Acid (MAA) | | 4.662 |
| Dimethylaminopropyl Methacrylamide (DMAPMA) | | 30.000 |
| Hydroxyethyl Methacrylate (HEMA) | | 65.000 |
| Trimethylolpropane trimethacrylate | | 0.300 |
| VAZO 52 | | 0.038 |
| Total (Polymer) | | 100.0 |
| Total Solids = | 20.00 | |
| Surfactant | 0.663 | |
| Ethyl Acetate/Cyclohexane = 54/46% wt | 79.337 | |
| Total | 100.00 | |

Example 3

Preparation of a HEMA/DMAPMA/MAA/DMAAm Polyampholyte in a Solvent Blend

| DMAPMA/MAA = 6.43% mol/mol | | |
|---|---|---|
| Reagent Name | % wt | % Mol |
| Methacrylic Acid (MAA) | | 4.662 |
| Dimethylaminopropyl Methacrylamide (DMAPMA) | | 30.000 |
| Hydroxyethyl Methacrylate (HEMA) | | 55.000 |

| DMAPMA/MAA = 6.43% mol/mol | | |
|---|---|---|
| Reagent Name | % wt | % Mol |
| Dimethyl Acrylamide (DMAAm) | | 10.00 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.663 | |
| Ethyl Acetate/Cyclohexane = 54/46% wt | 79.337 | |
| Total | 100.00 | |

Example 4

Preparation of a HEMA/DMAPMA/MAA Polyampholyte With a Long Chain Hydrophobic Monomer, SMA in a Solvent Blend

| DMAPMA/MAA = 8.19% mol/mol | | |
|---|---|---|
| Reagent Name | % wt | % Mol |
| Methacrylic Acid (MAA) | | 3.662 |
| Dimethylaminopropyl Methacrylamide (DMAPMA) | | 30.000 |
| Hydroxyethyl Methacrylate (HEMA) | | 65.000 |
| Stearyl Methacrylate (SMA) | | 1.00 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.652 | |
| Ethyl Acetate/Cyclohexane = 54/46% wt | 79.348 | |
| Total | 100.00 | |

Example 5

Preparation of a HEMA/DMAPMA/MAA Polyampholyte With a Long Chain Hydrophobic Monomer, SMA in a Solvent Blend

| DMAPMA/MAA = 11.27% mol/mol | | |
|---|---|---|
| Reagent Name | % wt | % Mol |
| Methacrylic Acid (MAA) | | 2.662 |
| Dimethylaminopropyl Methacrylamide (DMAPMA) | | 30.000 |
| Hydroxyethyl Methacrylate (HEMA) | | 65.000 |
| Stearyl Methacrylate (SMA) | | 2.00 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.641 | |
| Ethyl Acetate/Cyclohexane = 54/46% wt | 79.359 | |
| Total | 100.00 | |

Example 6

Preparation of a HEMA/HEA/DMAPMA/MAA Polyampholyte in a Solvent Blend

| DMAPMA/MAA = 6.43% mol/mol | | |
|---|---|---|
| Reagent Name | % wt | % Mol |
| Methacrylic Acid (MAA) | | 4.662 |
| Dimethylaminopropyl Methacrylamide (DMAPMA) | | 30.000 |
| Hydroxyethyl Methacrylate (HEMA) | | 55.000 |
| Hydroxyethyl Acrylate (HEA) | | 10.00 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.671 | |
| Ethyl Acetate/Cyclohexane = 54/46% wt | 79.329 | |
| Total | 100.00 | |

The $T_g$ of the resulting copolymer was 81° C.

Example 7

Preparation of a HEMA/DMAPMA/MAA Polyampholyte in a Solvent Blend

| DMAPMA/MAA = 6.43% mol/mol | | |
|---|---|---|
| Reagent Name | % wt | % Mol |
| Methacrylic Acid (MAA) | | 4.662 |
| Dimethylaminopropyl Methacrylamide | | 30.000 |
| Hydroxyethyl Methacrylate (HEMA) | | 65.000 |
| Trimethylolpropane Trimethacrylate | | 0.300 |
| VAZO 67 | | 0.038 |
| Total (Polymer) | | 100.0 |
| Total Solids = | 20.00 | |
| Surfactant | 0.663 | |
| Ethyl Acetate/Cyclohexane = 54/46% wt | 79.337 | |
| Total | 100.00 | |

The $T_g$ of the resulting copolymer was 83° C.

Example 8

Preparation of a MMA/DMAPMA/HEA/MAA Polyampholyte in a Solvent Blend

| DMAPMA/MAA = 6.42% mol/mol | | |
|---|---|---|
| Reagent Name | % wt | % Mol |
| Methacrylic Acid (MAA) | | 4.662 |
| Dimethylaminopropyl Methacrylamide | | 30.000 |
| Hydroxyethyl Acrylate (HEA) | | 10.00 |
| Methyl Methacrylate (MMA) | | 55.000 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.759 | |
| Ethyl Acetate/Cyclohexane = 54/46% wt | 79.241 | |
| Total | 100.00 | |

The $T_g$ of the resulting copolymer was 92° C.

Example 9

Preparation of a HEMA/DMAPMA/MAA Polyampholyte in a Solvent Blend

| DMAPMA/MAA = 6.42% mol/mol | | |
|---|---|---|
| Reagent Name | % wt | % Mol |
| Methacrylic Acid (MAA) | | 4.662 |
| Dimethylaminopropyl Methacrylamide | | 30.000 |
| Hydroxyethyl Methacrylate (HEMA) | | 65.000 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.663 | |
| Ethyl Acetate/Cyclohexane = 80/20 | 79.337 | |
| Total | 100.00 | |

The $T_g$ of the resulting copolymer was 88° C.

Example 10

Preparation of a HEMA/DMAPMA/HEA/MAA Polyampholyte in Ethyl Acetate Solvent

| DMAPMA/MAA = 6.42% mol/mol | | |
|---|---|---|
| Reagent Name | % wt | % Mol |
| Methacrylic Acid (MAA) | | 4.662 |
| Dimethylaminopropyl Methacrylamide | | 30.000 |
| Hydroxyethyl Acrylate (HEA) | | 10.00 |
| Hydroxyethyl Methacrylate (HEMA) | | 55.000 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.671 | |
| Ethyl Acetate | 79.329 | |
| Total | 100.00 | |

The $T_g$ of the resulting copolymer was 80.97° C.

Example 11

Preparation of a HEMA/DMAPMA/HEA/MAA Polyampholyte with Allyl Pentaerythritol as a Cross-Linker in a Ethyl Acetate DMAPMA/MAA = 6.43% mol/mol

| Reagent Name | % wt | % Mol |
|---|---|---|
| Methacrylic Acid (MAA) | | 4.662 |
| Dimethylaminopropyl Methacrylamide | | 30.000 |
| Hydroxyethyl Acrylate (HEA) | | 10.00 |
| Hydroxyethyl Methacrylate (HEMA) | | 55.000 |
| Allyl Pentaerythritol | | 0.300 |
| VAZO 52 | | 0.038 |
| Total (Polymer) | | 100.0 |
| Total Solids = | 20.00 | |
| Surfactant | 0.671 | |
| Ethyl Acetate/Cyclohexane | 79.329 | |
| Total | 100.00 | |

The $T_g$ of the resulting copolymer was 80.97° C.

Example 12

Preparation of a HEMA/DMAPMA/HEA/MAA Polyampholyte with a Siloxane-Glycol Surfactant in Ethyl Acetate DMAPMA/MAA = 6.43% mol/mol

| Reagent Name | % wt | % Mol |
|---|---|---|
| Methacrylic Acid (MAA) | | 4.662 |
| Dimethylaminopropyl Methacrylamide | | 30.000 |
| Hydroxyethyl Acrylate (HEA) | | 10.00 |
| Hydroxyethyl Methacrylate (HEMA) | | 55.000 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.400 | |
| Ethyl Acetate | 79.600 | |
| Total | 100.00 | |

Example 13

Preparation of a HEMA/DMAPMA/LEM-23/MAA Polyampholyte in a Solvent Blend

DMAPMA/MAA = 7.77% mol/mol

| Reagent Name | % wt | % Mol |
|---|---|---|
| Methacrylic Acid (MAA) | | 3.862 |
| Dimethylaminopropyl Methacrylamide | | 30.000 |
| Hydroxyethyl Methacrylate (HEMA) | | 65.000 |
| LEM-23 (*) | | 0.50 |
| Trimethylolpropane Methacrylate | | 0.600 |
| VAZO 52 | | 0.038 |
| Total (Polymer) | | 100.0 |
| Total Solids = | 20.00 | |

-continued

DMAPMA/MAA = 7.77% mol/mol

| Reagent Name | % wt | % Mol |
|---|---|---|
| Surfactant | 0.634 | |
| Ethyl Acetate/Cyclohexane = 54/46% wt | 79.366 | |
| Total | 100.00 | |

(*) LEM-23 is a polymerizable surfactant, ethoxylated (23 mole) lauryl alcohol methacrylate, sold by BIMAX, Inc., Cockeysville, MD.

Example 14

Preparation of a HEMA/DMAPMA/HEA/MAA Polyampholyte in Ethyl Acetate With Incremental Feed of Monomers DMAPMA/MAA = 6.43% mol/mol

| Reagent Name | % wt | % Mol |
|---|---|---|
| Methacrylic Acid (MAA) | | 4.662 |
| Dimethylaminopropyl Methacrylamide | | 30.000 |
| Hydroxyethyl Methacrylate (HEMA) | | 55.000 |
| Hydroxyethyl Acrylate (HEA) | | 10.00 |
| Trimethylolpropane Trimethacrylate | | 0.300 |
| VAZO 52 | | 0.038 |
| Total (Polymer) | | 100.0 |
| Total Solids = | 20.00 | |
| Surfactant | 0.679 | |
| Ethyl Acetate | 79.321 | |
| Total | 100.00 | |

However, the hydroxyethyl acetate (hydrophilic anionic monomer) was added in two equal parts in two stages. The second fraction of HEA was added one hour after the batch initiator was added. The $T_g$ of the resulting copolymer was 80.97° C.

Applications Testing

Samples of the copolymers of Examples 1–8 and 10–14 were evaluated in various applications to determine thickening efficiency as a function of pH and concentration of a cationic surfactant, e.g., cetrimonium chloride, CETAC. Gels were prepared, using 4% polymer by weight, in deionized water and neutralizing the polymer with acetic acid. Table 3 lists the measured solution viscosities in centipoise (cP) at 20 rpm as a function of pH. Table 4 lists the solution viscosities as a function of cetrimonium chloride concentration. In all application examples, the viscosity of the gel or mucilage was measured using a Brookfield viscometer RV, spindle #6 at 200 rpm and at 25° C. temperature.

TABLE 3

VISCOSITY AS A FUNCTION OF pH

| Polymer Example | pH nominal | 10 | 9 | 8 | 7 | 6 | 5 | 4 | 3 |
|---|---|---|---|---|---|---|---|---|---|
| 1 | pH actual | 9.64 | 8.96 | 7.99 | 7.00 | 5.90 | 5.02 | 4.07 | 3.45 |
|   | Viscosity | 6,100 | 500 | 24,500 | 39,450 | 47,000 | 42,600 | 58,000 | 58,000 |
| 2 | pH actual | 10.07 | 8.97 | 8.01 | 7.09 | 5.88 | 5.03 | 4.10 | 3.55 |
|   | Viscosity | 900 | 900 | 26,000 | 39,000 | 45,000 | 46,000 | 51,000 | 58,000 |
| 3 | pH actual | 9.80 | 8.98 | 8.01 | 7.04 | 6.00 | 5.25 | 4.20 | 3.80 |
|   | Viscosity | 2,300 | 1,500 | 18,300 | 25,500 | 26,000 | 28,100 | 30,750 | 33,100 |
| 4 | pH actual | 10.01 | 9.05 | 8.01 | 6.92 | 5.80 | 5.00 | 4.10 | 3.64 |
|   | Viscosity | <500 | <500 | 28,000 | 35,700 | 43,000 | 43,500 | 45,000 | 48,500 |
| 5 | pH actual | 10.20 | 9.06 | 8.06 | 7.10 | 6.00 | 5.15 | 4.18 | NA |
|   | Viscosity | NA | 38 | 11,320 | 42,500 | 41,000 | 39,800 | 39,000 | NA |
| 6 | pH actual | 9.41 | 8.90 | 8.02 | 6.70 | 5.89 | 4.90 | 4.17 | 3.50 |
|   | Viscosity | 1,330 | 1,270 | 27,600 | 35,000 | 40,000 | 46,000 | 66,000 | 52,000 |
| 7 | pH actual | 9.80 | 9.01 | 8.00 | 7.00 | 6.10 | 4.90 | 3.85 | NA |
|   | Viscosity | NA | 850 | 32,350 | 35,000 | 37,000 | 40,000 | 57,000 | NA |
| 8 | pH actual | NA | 9.21 | 7.98 | 6.91 | 5.99 | 4.98 | 4.01 | 3.50 |
|   | Viscosity | NA | NA | 100 | 101 | 3,900 | 9,300 | 13,200 | 15,000 |
| 10 | pH actual | 9.40 | 9.10 | 8.15 | 7.00 | 6.00 | 4.85 | 4.10 | 3.48 |
|   | Viscosity | NA | 50 | 17,000 | 18,500 | 20,500 | 22,500 | 27,500 | 30,300 |
| 11 | pH actual | 9.45 | 8.91 | 8.16 | 7.15 | 5.89 | 5.14 | 4.20 | NA |
|   | Viscosity | NA | 2,015 | 5,300 | 5,930 | 5,730 | 5,400 | 4,730 | NA |
| 12 | pH actual | NA | 9.4 | 8.00 | 6.95 | 6.00 | 4.99 | 4.11 | 3.47 |
|   | Viscosity | NA | NA | 4,800 | 12,700 | 17,400 | 21,300 | 26,200 | 27,500 |
| 13 | pH actual | 9.68 | 8.98 | 7.90 | 7.05 | 5.52 | 5.15 | 4.13 | 3.50 |
|   | Viscosity | 160 | 160 | 21,100 | 32,650 | 33,000 | 38,100 | 49,000 | 40,000 |
| 14 | pH actual | NA | 9.23 | 8.15 | 6.53 | 5.85 | 5.10 | 3.92 | 3.45 |
|   | Viscosity | NA | NA | 9,340 | 23,500 | 25,500 | 25,500 | 33,000 | 34,300 |

NA = Not measured

TABLE 4

VISCOSITY (cP) AS A FUNCTION OF % BY WT ACTIVE CETRIMONIUM CHLORIDE

| Polymer | pH | 0% | 1.00% | 2.00% | 3.00% | 4.00% | 5.00% | 6.00% |
|---|---|---|---|---|---|---|---|---|
| 2 | 4.80 | 41,000 | 34,100 | 23,100 | 16,000 | 9,740 | 7,340 | 5,090 |
| 3 | 4.95 | 47,000 | 33,000 | 22,250 | 12,940 | 8,900 | 5,880 | 4,360 |
| 4 | 5.10 | 25,500 | 21,500 | 13,400 | 8,360 | 5,760 | 4,520 | 3,440 |
| 5 | 5.02 | 47,000 | 35,500 | 24,500 | 15,600 | 9,620 | 7,020 | 5,180 |
| 6 | 5.25 | 38,000 | 38,400 | 27,000 | 15,100 | 9,250 | 5,300 | NA |
| 7 | 4.45 | 39,600 | 29,000 | 19,400 | 14,500 | 9,840 | 7,450 | NA |
| 8 | 4.46 | 42,000 | 30,500 | 15,500 | 11,400 | 7,400 | 5,500 | NA |
| 12 | 4.70 | 5,540 | 2,760 | 1,700 | 1,280 | 1,045 | 875 | NA |
| 14 | 4.51 | 39,200 | 26,700 | 16,300 | 11,100 | 6,720 | 6,640 | NA |

NA = Not measured

As seen from Tables 3 and 4, the polymers exhibited high viscosity over a wide range of pH and at relatively high concentrations of cationic surfactant.

Example 15

Preparation of a DMAEMA/NVP/AA/SMA Polyampholyte in a Cyclohexane Solvent 4.43 g of N,N dimethylaminoethyl methacrylate (DMAEMA), 124.33 g of N-vinyl pyrrolidone (NVP), 4.31 g of stearyl methacrylate (SMA), and 0.90 g of ethylene glycol dimethacrylate, a cross-linking agent, were charged into a reactor, together with 543 g of a solvent, cyclohexane. The reactor was purged with nitrogen overnight. The reactor was heated to about 75° C., while stirring. 2.03 g of acrylic acid were dissolved in a further 100 g of solvent and purged with nitrogen. The acrylic acid/solvent mixture was added to the reactor at a rate of 2 ml/min. After 10 minutes, 0.388 g of a batch initiator, Vazo 67 (2,2'-azobis(2-methylbutyronitrile), sold by DuPont) was added to the reactor. The reactor was held at 75° C. for eight hours. 0.5 g of the Vazo 67 was then added as a kick initiator and continued reacting 2 more hours. The contents of the reactor were transferred to a rotary evaporator and dried at 105° C. overnight.

The muscilage viscosity of the copolymer at 4% by weight in deionized water formed was tested in the presence of 2% sodium hydroxide at pH 9.00. The viscosity was 10,800 cP.

Evaluation

Mucilages of the copolymer of Example 15 were prepared by adding 4% by weight of the copolymer to water at 45–50° C., while stirring. The pH of the resulting dispersion was 5.84. The viscosity of the mucilage was measured over a range of pH from 6–13. Table 5 shows the viscosity dependence on pH.

TABLE 5

Viscosity dependence upon pH at 4.0% resin concentration

| pH | Viscosity (cP) |
| --- | --- |
| 5.84 | 1,100 |
| 6.87 | 2,490 |
| 7.94 | 20,300 |
| 8.85 | 35,500 |
| 10.16 | 50,600 |
| 11.88 | 15,200 |
| 12.9 | 3,300 |

Next, samples of the polymer of Example 15 were tested with CETAC, a cationic surfactant. Cetrimonium chloride was added to a 4% by weight dispersion of the polymer in increments of 1%, while stirring at a rate of 20 rpm. Table 6 provides the viscosities of duplicate samples of the polymer for additions of centrimonium chloride between 0 and 5% by weight.

TABLE 6

| CETAC LEVEL | VISCOSITY (cP) | |
| --- | --- | --- |
| % wt | TRIAL 1 | TRIAL 2 |
| 0.00 | 1,100 | 1,330 |
| 1.00 | 14,300 | 15,500 |
| 2.00 | 4,000 | 3,980 |
| 3.00 | 1,270 | 1,985 |
| 4.00 | 730 | 1,205 |
| 5.00 | 550 | 830 |

As seen from Table 6, viscosity improved in the presence of around 1% cetrimonium chloride, and remained relatively high, even at increased levels of cetrimonium chloride. Viscosity of CETAC-containing systems in presence of the polymer (Example 15) was above control (no CETAC) up to and slightly more than 3%.

Example 16

Preparation of a DMAEMA/NVP/AA/Methoxypoly(ethyleneoxy)-40-ethyl Acrylate Polyampholyte in Cyclohexane The process of Example 15 was used to prepare the copolymer. Prior to addition of the remaining ingredients, the reactor was charged with methoxypoly(ethyleneoxy)-40-ethyl acrylate. The ingredients were added in the following amounts:

| Reagent Name | % wt |
| --- | --- |
| Acrylic Acid (AA) | 0.254 |
| N,N Dimethylaminoethyl Methacrylate (DMAEMA) | 0.554 |
| N-Vinyl Pyrrolidone (NVP) | 15.572 |
| Stearyl Methacrylate (SMA) | 0.270 |
| Allyl Pentaerythritol (APE) | 0.094 |
| Methoxypoly(ethyleneoxy)-40-ethyl Acrylate | 0.256 |
| TOTAL SOLIDS = | 17.00 |
| Cyclohexane | 82.976 |
| Vazo 67 - Initiator | 0.024 |
| TOTAL SOLVENT + INITIATOR = | 83.00 |
| TOTAL = | 100.00 |

The resulting copolymer had a viscosity of 7550 cP when tested with 2% sodium hydroxide at pH 9.23.

Example 17

Preparation of a DMAEMA/VP/AA/SMA Polyampholyte in Cyclohexane

The process of Example 15 was used to prepare the copolymer, except that the cross-linker was metered into the reactor with the acrylic acid. The ingredients were added in the following amounts:

| Reagent Name | % wt |
| --- | --- |
| Acrylic Acid (AA) | 0.260 |
| N,N Dimethylaminoethyl Methacrylate (NDAEMA) | 0.142 |
| N-Vinyl Pyrrolidone (NVP) | 15.935 |
| Stearyl Methacrylate (SMA) | 0.552 |
| Ethylene Glycol Dimethacrylate | 0.111 |
| TOTAL SOLIDS = | 17.00 |
| Cyclohexane | 82.950 |
| Vazo 67 - Initiator | 0.050 |
| TOTAL SOLVENT + INITIATOR = | 83.00 |
| TOTAL = | 100.00 |

The resulting copolymer had a viscosity of 18,750 cP when tested with 2% sodium hydroxide at pH 9.71.

Example 18

Preparation of a Methacrylamide-Based Polyampholyte

| Reagent Name | % wt | % Mol |
| --- | --- | --- |
| Methacrylamide (MAM) | | 74.362 |
| Dimethylaminopropyl Methacrylate (DMAPMA) | | 20.00 |
| Methacrylic Acid (MAA) | | 5.00 |
| Methylene Bisacrylamide | | 0.60 |
| VAZO 52 | | 0.038 |
| Total Solids = | 20.00 | |
| t-butyl Alcohol/Water (96/4% wt) | 80.00 | |
| Total | 100.00 | |

The copolymer was isolated as a powder. A 2.0% wt of this powder was dispersed in water and neutralized with acetic acid to pH=4.22. This gave a "buttery", non-tacky, clear mucilage with a viscosity of 31,000 cP, and excellent aesthetic properties.

Example 19

Preparation of a Methacrylamide-Based Polyampholyte with a Polymerizable Surfactant, Stearyl Methacrylate

| Reagent Name | % wt | % Mol |
| --- | --- | --- |
| Methacrylamide | | 73.862 |
| Dimethylaminopropyl Methacrylate (DMAPMA) | | 20.000 |
| Methacrylic Acid (MAA) | | 5.000 |
| Methylene Bisacrylamide | | 0.600 |
| Stearyl Methacrylate (SMA) | | 0.500 |
| VAZO 52 | | 0.038 |

| Reagent Name | % wt | % Mol |
|---|---|---|
| Total | | 100.0 |
| Total Solids = | 20.00 | |
| t-butyl Alcohol/Water (96/4% wt) | 80.00 | |
| Total | 100.00 | |

The copolymer was isolated as a powder. A 1.0% by wt. of this powder was dispersed in water and neutralized with acetic acid to pH=4.04. This gave a "buttery", non-tacky, clear mucilage having a viscosity of 34,250 cP, and excellent aesthetic properties. A 2.0% by wt. copolymer in water at low pH gave mucilage viscosity greater than 80,000 cP.

FURTHER APPLICATION EXAMPLES

Example 20

Thickened Organic Acid Formulation

The copolymer of Example 6 was used to prepare a thickened, organic acid formulation shown below:

| MATERIALS | % wt |
|---|---|
| Polymer of Example 6 | 2.00 |
| Lactic acid (88% wt solution in water) | 28.00 |
| Deionized water | QS to 100.00% |

To prepare the formulation, the copolymer was slowly added to the water while agitating in a laboratory mixer. After 15 minutes mixing, lactic acid was added to the agitating dispersion bring the acid content to 24.6% by weight of acid. The resulting formulation had the appearance of a hazy gel and had a pH of 1.78 and a viscosity of 9,600 cP.

Example 21

Hair Conditioning Formulation

The copolymer of Example 18 was used in the preparation of a hair conditioning formulation in the following proportions:

| MATERIALS | % wt |
|---|---|
| Copolymer of Example 18 | 2.00 |
| Cetrimonium Chloride | 10.00 |
| Propylene Glycol | 8.00 |
| Myristyl Alcohol | 2.00 |
| Decyl Oleate | 1.50 |
| Citric Acid | 1.00 |
| Preservative | 1.00 |
| Deionized Water | QS to 100.00% |

To prepare the hair conditioning formulation, the copolymer was dispersed in water under agitation. The mixture was heated to 80° C. while mixing was continued. The other ingredients, with the exception of the preservative, were heated to 80° C. in a separate vessel, with low agitation. The contents of the two vessels were combined with rapid agitation and then cooled to room temperature. Citric acid was added as necessary to achieve a desired pH and viscosity. The preservative (DMDM Hydantoin which is available from Lonza Chemicals as Glydant preservative) was added. The formulation had a white cream appearance, a pH of 3.85, and a viscosity of 13,400 cP.

Example 22

Combined Shampoo and Conditioning Formulation

The copolymer of Example 18 was used in the preparation of a hair conditioning and shampoo formulation having the following composition:

| MATERIALS | % wt |
|---|---|
| Sodium Laureth Sulfate | 35.00 |
| Disodium Laureth Sulfosuccinate | 8.00 |
| Cocamidopropyl Betaine | 5.00 |
| Copolymer of Example 18 | 2.00 |
| Lactic Acid | .60 |
| Citric acid | 1.00 |
| Deionized water | QS to 100.00% |

To prepare the hair conditioning formulation, the sodium laureth sulfate was added to a mixture of the citric acid and water and mixed until homogeneous. The disodium laureth sulfosuccinate and cocamidopropyl betaine were then added with continued mixing. The copolymer was added to the mixture with agitation and allowed sufficient time to hydrate and swell. Citric acid was added to adjust the pH. The resulting formulation had an opaque appearance, a pH of 4.5, and a viscosity of 3,850 cP.

Example 23

Preparation of a Fabric Softener Formulation

A fabric softener formulation was prepared having the following composition:

| MATERIALS | % wt |
|---|---|
| Copolymer of Example 18 | 1.00 |
| Dimethyl Dialkyl Ammonium Chloride | 5.30 |
| Acetic Acid | 0.25 |
| Fragrance | 0.50 |
| Deionized water | QS to 100.00% |

To prepare the formulation, the copolymer was first added to water while heating under agitation. The dimethyl dialkyl ammonium chloride was added when the temperature reached 65° C. The mixture was allowed to cool for ten minutes with continued mixing. The acetic acid was added and the sample cooled to 35° C. The fragrance was then added. The formulation produced had an opaque appearance, a pH of 4.55, and a viscosity of 11,000 cP.

Example 24

Leave-on Hair Conditioning Formulation

A leave-on hair conditioning formulation was prepared. In a formulation vessel, the copolymer of Example 10 (1.5 wt. %) was dispersed in deionized water (68.7 wt. %) while agitating the dispersion at around 800 rpm. The dispersion was heated to between 55 and 60° C. before adding glycerin (2.0 wt. %). In a separate vessel, cetyl alcohol (1.75 wt %) and jojoba oil (0.25 wt. %) were heated to 60° C. This mixture was then added to the formulation vessel with agitation at 60° C. The heat was removed and agitation continued. Once the mixture cooled, lactic acid (0.30 wt. %) was added at around 45° C. In a separate vessel, cocamidopropyl dimethylamine (1.5 wt. %), citric acid (1.0 wt. %), and deionized water (10.0 wt. %) were mixed until dissolved and then it was added to the formulation vessel. In a separate vessel, distearyldimonimum chloride (2.0 wt. %) was mixed with deionized water (10.0 wt %) and then the mixture added to the formulation vessel. Once the sample cooled to 30° C. a preservative was added (1.0 wt. %).

The formulation had a viscosity of about 5,000 cP. The formulation readily spread on the hair, improving manageability and ease of detangling.

Example 25

Leave-on Hair Conditioning Formulation

The procedure of Example 24 was used in preparing a leave-on hair conditioning formulation using the copolymer of Example 19.

Similar properties were observed to those of the formulation of Example 24.

Example 26

Leave-on Hair conditioning Formulation for Colored, Bleached or Damaged Hair A formulation for treatment of colored, bleached or damaged hair was prepared using the following formulation:

| MATERIAL | % wt |
| --- | --- |
| Deionized Water | QS to 100.00% |
| Copolymer of Example 10 | 1.50 |
| Glycerin | 1.00 |
| Lactic Acid | 0.30 |
| Cetyl Alcohol | 2.00 |
| Cetrimonium chloride | 5.00 |
| Hydrolysed Wheat Protein | 0.25 |
| Preservative (DMDM Hydantoin) | 1.00 |
| Total | 100.00 |

To prepare the formulation, the copolymer of Example 10 was dispersed in disodium EDTA with water with agitation at 800 rpm. Glycerin was added, and mixed for 20 minutes. The dispersion was heat to around 55° C. and lactic acid added. In separate vessel, cetyl alcohol and cetrimonium chloride were combined and heated to 55° C. Once these were melted, they were added to the formulation vessel. The mixture was cooled to 40° C. before adding first hydrolyzed wheat protein (which is available from Croda, Niles, Ill.) and then the preservative. The formulation was mixed until smooth. The formulation had viscosity of about 4,000 cP. It was easy to spread on damaged hair, improving manageability and detangling. This formulation demonstrates the ability of the copolymers to tolerate extremely high levels of cationic ingredients. When the formulation test was repeated using the copolymer of Example 18, the results were the same.

Example 27

Two-in-One Shampoo Conditioner Formulation

A two-in-one shampoo and conditioner formulation was prepared with the following ingredients:

| MATERIAL | % wt |
| --- | --- |
| Deionized Water | QS to 100.00% |
| Disodium EDTA | 0.10 |
| Copolymer of Example 10 | 1.50 |
| Stearamidopropyl Dimethylamine | 2.50 |
| Citric Acid (50% wt. in water) | 2.00 |
| Cocamidopropyl Betaine | 5.00 |
| Lactic Acid | 0.25 |
| Sodium Lauryl Ether Sulfate | 30.00 |
| Preservative (DMDM Hydantoin) | 1.00 |
| Total | 100.00 |

To prepare the formulation, the copolymer of Example 10 was dispersed in disodium EDTA dissolved in 57.65% wt. of water solution and agitation at 800 rpm in a formulation vessel. The dispersion was mixed for 20 minutes. In a separate vessel, stearamidopropyl dimethylamine and citric acid were combined with a further 10.0 wt % water, and mixed until solubilized. This mixture was then added to the formulation vessel. Cocamidopropyl betaine was then added, followed by lactic acid. Sodium lauryl ether sulfate was added with slow agitation at around 300 rpm. Finally, preservative was added to the formulation.

This formulation demonstrates the compatibility of the copolymer with both amphoteric and anionic surfactants.

Example 28

Two-in-One Shampoo Conditioner Formulation with Cationic Polymers

Two-in-One shampoo and conditioner formulations were prepared using the following ingredients:

| MATERIAL | % wt |
| --- | --- |
| Deionized Water | QS to 100.00% |
| Disodium EDTA | 0.10 |
| Copolymer of Example 10 | 1.50 |
| Jaguar C12-S | 0.50 |
| Stearyl Alcohol | 1.50 |
| Sodium Sulfosuccinate | 6.00 |
| Ammonium Laureth Sulfate | 30.00 |
| Lactic Acid | 0.25 |
| Cocamidopropylamine Oxide | 2.00 |
| Preservative (DMDM Hydantoin) | 1.00 |
| Total | 100.00 |

To prepare the formulation, the copolymer of Example 10 was dispersed in 47.15 wt. % of deionized water and disodium EDTA in a formulation vessel. Jaguar C12-S, which is Guar hydroxypropyl trimoniumchloride supplied by Rhone Poulenc, and stearyl alcohol were added to the formulation vessel. The mixture was heated to 65° C. Once the alcohol had melted, the heat was removed and agitation continued. The sample was cooled to 30° C. and sodium sulfosuccinate and ammonium laureth sulfate added in order. Lactic acid was then added. In a separate vessel, cocamidopropylamine oxide was mixed with a further 10 wt. % of deionized water and added to the formulation vessel under agitation. Finally, preservative was added.

The formulation had viscosity of about 5,000 cP. They are easy to spread on hair, have good foaming and lathering properties, and improve the manageability and detangling of the hair. This formulation demonstrates the compatibility of the copolymer with cationic polymers and anionic surfactants.

When repeated with the copolymer of Example 18, the same results were obtained.

Example 29

Clear Gel Hair Conditioner

A clear gel hair conditioner was prepared using the following ingredients:

| MATERIALS | % wt |
|---|---|
| Deionized Water | QS to 100.00% |
| Celquat L-200 | 0.20 |
| Copolymer of Example 18 | 1.50 |
| PVP/VA Copolymer | 6.00 |
| Soluble Wheat Protein | 0.20 |
| Dimethicone Copolyol (DC 193) | 0.80 |
| Lactic Acid 88% | 0.40 |
| Glydant | 0.30 |

To prepare the hair conditioner, the copolymer of Example 18 was dispersed with Celquat® L-200, which is a poly quaternium 4 supplied by National Starch, Bridgewater, N.J., and deionized water and mixed for 20 minutes. The remaining ingredients were then added in order. Dimethicone copolyol, DC 193, is supplied by Dow Corning, Midland, Mich. PVP/NVA copolymer is polyvinylpyrrolidone/vinylacetate copolymer supplied by ISP, International.

The formulation had a viscosity of about 5,000 cP. It is easy to spread on the hair and provides good hairstyling properties by improving the manageability of the hair.

Example 30

Rinse-off, Cationic Silicone-Based Hair Conditioning Formulation

A hair conditioning formulation was prepared using the following ingredients:

| MATERIAL | % wt |
|---|---|
| Copolymer of Example 10 | 1.50 |
| Propylene Glycol | 2.00 |
| Myristyl Alcohol | 2.00 |
| Behentrimonium Chloride | 1.50 |
| Lactic Acid | 0.30 |
| Hydrolyzed Protein | 0.15 |
| Amodimethicone | 2.00 |
| Preservative | 1.00 |
| Deionized Water | QS to 100.00% |

The hair conditioning formulation was prepared by dispersing the copolymer of Example 10 in deionized water and then agitating at around 800 rpm in a formulation vessel. The dispersion was heated to 70° C. Propylene glycol was added while heating.

In a separate vessel, myristyl alcohol and behentrimonium chloride were combined and heated to around to 70 to 75° C. until melted. The combination was then added to the formulation vessel at around 70° C. while mixing at 500 to 800 rpm. The mixture was cooled to around 40° C. before adding lactic acid. Hydrolyzed protein and amodimethicone (which is a polymer supplied by Dow Corning, Midland, Mich.) were added slowly, in order. Finally, preservative was added.

The formulations had a viscosity of about 4,000 cP. They are easy to spread on hair, have good rinseability and improve the manageability and wet detangling of the hair. When this example was repeated using the polymer of Example 18, the results were the same. This example demonstrates the compatibility of the copolymers with cationic dimethyl siloxane conditioning polymers.

Example 31

Thickening Efficiency with Amino Acids and Base

The following examples demonstrate the usefulness of the ampholytic polymers of this invention. Because of their ampholytic character they can be neutralized with either acids, bases, or amino acids to achieve optimum thickening of aqueous or alcoholic formulations.

The following copolymer was used for this test. It was prepared according to the method of Example 10, with the following composition:

| INGREDIENTS | % Mol |
|---|---|
| Hydroxyethyl Methacrylate (HEMA) | 55.00 |
| Dimethylaminopropyl Methacrylamide | 26.00 |
| Methacrylic Acid | 8.154 |
| Hydroxyethyl Acrylate, (HEA) | 10.00 |
| Trimethylolpropane Trimethacrylate | 0.600 |
| Stearyl Methacrylate (SMA) | 0.200 |
| VAZO 52 | 0.046 |
| Total | 100.00 |

The copolymer was dispersed in deionized water and then neutralized with one of the acids and bases listed in Examples A–F in Table 11 below.

TABLE 7

| | Example A | Example B | Example C | Example D | Example E | Example F |
|---|---|---|---|---|---|---|
| Deionized Water (Grams) | 98.00 | 98.00 | 98.00 | 98.00 | 98.00 | 98.00 |
| Copolymer (Grams) | 2.00 | 2.00 | 2.00 | 2.00 | 2.00 | 2.00 |
| L-Arginine (Grams) | 1.00 | | | | | |

TABLE 7-continued

|  | Example A | Example B | Example C | Example D | Example E | Example F |
|---|---|---|---|---|---|---|
| L-Serine (Grams) |  | 2.00 |  |  |  |  |
| L-Aspartic Acid (Grams) |  |  | 1.00 |  |  |  |
| Salicylic Acid (Grams) |  |  |  | 1.00 |  |  |
| Sodium hydroxide (18% wt. in water) (Grams) |  |  |  |  | .025 |  |
| Aminomethylpropanol (95% in water) (Grams) |  |  |  |  |  | 0.20 |
| pH | 9.50 | 7.44 | 3.81 | 3.00 | 9.75 | 9.60 |
| Viscosity cP | 3,000 | 790 | 12,000 | 2,200 | 5,600 | 4,500 |

The neutralized dispersion was a stable, thickened mixture. Without neutralization or mixing, the copolymer, which is dispersed in the deionized water, separates into two phases.

Example 32

Use of the Copolymer in Hydroalcoholic and Alcoholic Systems

A copolymer was prepared by the method of Example 10, with the following composition:

| INGREDIENT | % Mol |
|---|---|
| Hydroxyethyl Methacrylate (HEMA) | 55.00 |
| Dimethylaminopropyl Methacrylamide | 26.00 |
| Methacrylic Acid | 8.454 |
| Hydroxyethyl Acrylate (HEA) | 10.00 |
| Trimethylolpropane Trimethacrylate | 0.500 |
| Vazo 52 | 0.046 |
| Total | 100.00 |

Hydroalcoholic and alcoholic systems A–G were prepared as follows using the copolymer.

| Hydro-alcoholic systems | Example A | Example B | Example C |
|---|---|---|---|
| Deionized Water % wt. | QS | QS | QS |
| Copolymer % wt. | 2.00 | 2.00 | 2.00 |
| Ethanol % wt. | 50.00 |  |  |
| Isopropyl Alcohol % wt. |  | 50.00 |  |
| Propylene Glycol % wt. |  |  | 50.00 |
| Lactic Acid (88%) % wt. | 0.40 | 0.40 | 0.40 |
| PH | 5.00 | 4.98 | 5.04 |
| Viscosity (cP) | 10,300 | 7,700 | 13,940 |

| Alcoholic Systems | Example D | Example E | Example F | Example G |
|---|---|---|---|---|
| Ethanol % wt. | 97.00 |  |  |  |
| Copolymer % wt. |  | 97.00 |  |  |
| Ethanol % wt. | 50.00 |  | 97.00 |  |
| Isopropyl Alcohol % wt. |  | 50.00 |  | 97.00 |
| Propylene Glycol % wt. |  |  |  | 2.00 |
| Lactic Acid (88%) % wt. | 0.40 | 0.40 | 1.00 | 1.00 |
| pH | 5.00 | 4.98 |  | 5.04 |
| Viscosity (cP) | 10,300 | 7,700 |  | 13,940 |

Example 33

Phosphate Removal by the Copolymer

The phosphate removing capacity of the copolymer was tested over a range of pH. A known amount (1 to 3 g) of the copolymer was added to distilled water and the dispersed copolymer stirred for 15 minutes at 500 to 800 rpm. The pH of the polymer dispersion was adjusted to a selected value (4.5 or 7.0) with sodium carbonate and 50% wt. citric acid in water. Sodium chloride and sodium phosphate, at final concentrations of 45.0 mM and 6.25 mM, respectively, were added to the dispersion and the mixture stirred for three hours at room temperature. The dispersion was centrifuged for 15 minutes at 5,000 g in plastic centrifuge tube and the phosphate concentration in the supernatant analyzed spectrophotometrically according to the procedure described in U.S. Pat. No. 4,889,637. The molar ratios of monomers for two of the copolymers evaluated are listed in Table 8.

TABLE 8

Composition of Copolymers Evaluated

| Polymer | % Mol | | | |
|---|---|---|---|---|
|  | HEMA | DMAPMA | HEA | MAA |
| A* | 55 | 30 | 10 | 5 |
| B** | 50 | 30 | 10 | 10 |

HEMA: hydroxyethyl methacrylate; DMAPMA: dimethylaminopropyl methacrylamide;
HEA: hydroxyethyl acrylate; MAA: methacrylic acid
*Crosslinker - allylpentaerythritol (APE);
**Crosslinker - trimethylolopropane trimethacrylate (TMPTMA)

The phosphate removing capacity of these copolymers is shown in Table 8.

TABLE 9

Phosphate Removal Capacity of Copolymers

| Polymer | 1% Polymer Concentration | | | 4% Polymer Concentration | |
|---|---|---|---|---|---|
|  |  | Phosphate Removed | |  | Phosphate Removed |
|  | Ph | (wt %) | meq/g | pH | (wt %) |
| A | 7.0 | 8.8* | 0.17 | 7.0 | 21.3* |
| B | 7.0 | 13.9* | 0.27 | 7.0 | 30.2* |
| A | 4.5 | 24.3** | 0.46 | 4.5 | 48.6** |

*$Na_2CO_3$ = 6.0 mM
**$Na_2CO_3$ = 0.0 mM

As seen from Table 9, the amphopholytic copolymers show excellent phosphate removing properties from aqueous solutions at both neutral and akaline pH. This can be contrasted with, e.g., Maalox® Extra Strength liquid, which is an aluminum hydroxide/magnesium hydroxide based material and is commercially available from Ciba Self Medication, Inc., which achieves a phosphate removal of 0.56 meq/g (milliequivalents per gram) at a pH of 7.0. Further, U.S. Pat. No. 5,667,775 discloses a polymer for use in phosphate removal and achieves a removal of from about 0.1 to 0.31 meq/g.

Example 34

Bioadhesion Properties of the Copolymer

The bioadhesive (or mucoadhesive) properties of the copolymer were tested using pellets formed from the copolymer on samples of pig stomach. Pig stomach is widely used in simulating the membranes of the gastrointestinal system of both humans and other animals. See, for example, Tobyn, M. J. et al, "Factors affecting in vitro gastric mucoadhesion. I. Test conditions and instrumental parameters.", Eur. J. Pharm. Biopharm., 41 (1995) 235–241. Simulated gastric fluid (SGF) and simulated intestinal fluid (SIF) were prepared using chemicals and deionized-distilled water according to standard recipes. Pellets of the copolymer at 0.2 g weight were prepared by compressing the copolymer at two tons in a 13 mm KBr die. The pellets were affixed to a stainless steel probe 13 mm wide and 41 mm in length using 3M Scotch Wallsaver removal poster tape, 19 mm wide. The edges of the poster tape were held tightly to the shaft of the probe with 3M Outdoor Window Film Mounting Tape to add extra security.

The bioadhesion experiments were carried out at room temperature and at 1.0 atmosphere. A small pig stomach section (approximately 13cm$^2$) was soaked in SIF (Simulated Intestinal Fluid, pH −7.5) or SGF (Simulated Gastric Fluid, pH −1.2) for 20 minutes and then carefully transferred to a test cell. The cell was filled with 2.5 mL SGF or SIF at room temperature. The pellet to be tested was affixed to the probe and lowered into the cell, being careful to ensure that there were no air bubbles under the pellet that could interfere with the contact area. The pellet was held against the section of pig stomach at a force of 0.5N for six minutes. The bioadhesion capacity (or work of adhesion) on the pigs stomach in both SGI and SGF was measured using TA-X2 Texture Analyzer and analyzed with Texture Expert software. Table 9 compares the bioadhesion capacity of the two copolymers A and B used in Example 34 with Carbopol 934 acrylic acid polymer, a neutral copolymer, poly (N-vinylpyrrolidone), and chitosan, which is a natural polymer.

TABLE 10

| Copolymer | Bioadhesion capacity (expressed as work of adhesion or gram seconds (g s)) | |
|---|---|---|
| | SGF (pH of 1.2) | SIF (pH of 7.5) |
| A | 399 | 258 |
| B | 165 | 418 |
| C | 302 | 453 |
| D | 21 | 20 |
| E | 241 | — |

Polymer C: Carbopol 934 polymer, Polymer D: poly (N-vinylpyrrolidone), Polymer E: chitosan Table 10 clearly shows that the copolymer compositions A and B are effective bioadhesion materials. The copolymers are effective in both the acidic conditions of the gastric fluid and in the close to neutral or alkaline conditions of the intestinal fluid. In contrast, the non-ionic polymer, poly (N-vinylpyrrolidone), exhibits poor bioadhesiveness to pig stomach in both SGI and SIF, while Carbopol 934, which is a crosslinked acrylic acid polymer, and chitosan exhibit good bioadhesion.

Because of the known correlation of pig stomach with human and animal gastro-intestinal membranes, it is reasonable to infer that similar results would be obtained in vivo, both in humans, and in other animals. Bioadhesive polymers can be used to treat mucosal or skin dryness and to deliver drugs via transmucosal and transdermal applications and devices. Examples of such uses can be found in U.S. Pat. No. 5,744,155 to D. Freidman et al, which is incorporated herein by reference and which lists drugs which can be delivered via the polymers of the present invention. Other applications include nasal delivery of antiviral drugs, sustained delivery of drugs, topical ointments, and vaginal delivery of drugs.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A hydrophilic ampholytic polymer formed by copolymerization of:

0.05 to 20 mole percent of an anionic monomer having at least one carboxy-functional group;

10 to 45 mole percent of a non-quaternized cationic monomer having at least one amino-functional group;

35 to 95 mole percent of a non-ionic hydrophilic monomer;

0.5 to 10 mole percent of a hydrophobic monomer; and, 0 to 1.5 mole percent of a cross-linking monomer, and wherein the monomers are selected so as to provide the copolymer with a glass transition temperature of above about 50° C. and the non-quaternized cationic monomer to the anionic monomer ratio is from about 2:1 to about 16:1.

2. The copolymer of claim 1, wherein the anionic monomer is at a concentration of 0.05–20 mole percent.

3. The copolymer of claim 1, wherein the non-quaternized cationic monomer is at a concentration of 10–45 mole percent.

4. The copolymer of claim 1, wherein the non-quaternized cationic monomer to the anionic monomer ratio is from about 3:1 to about 16:1, and wherein the hydrophobic monomer is used in an amount of less than 2 mole percent.

5. The copolymer of claim 1, wherein the non-ionic hydrophilic monomer is at a concentration of 35–95 mole percent.

6. The copolymer of claim 5, wherein the non-ionic hydrophilic monomer is at a concentration of 55–75 mole percent.

7. The copolymer of claim 1, wherein the cross-linking monomer is at a concentration of 0.005–1.5 mole percent.

8. The copolymer of claim 1, wherein the anionic monomer is an ethylenically unsaturated carboxylic acid selected from the group consisting of the following structures:

(A)

-continued

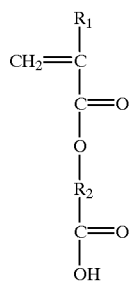
(B)

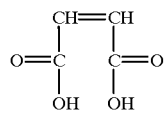
(C)

where
R$_1$=—H, —CH$_3$, —CH$_2$CH$_3$
R$_2$=—(CH$_2$—)$_n$, where n=1 to 40, linear or branched alkyl, cycloalkyl, aryl, a polyethylene oxide chain having the formula —(CH$_2$—CH$_2$—O)$_p$— where p=1 to 50, or a polypropylene oxide chain having the formula —(CH$_2$(CH$_3$)—CH$_2$—O)$_p$— where p=1 to 100.

9. The copolymer of claim 1, wherein the anionic monomer is selected from the group consisting of acrylic acid, methacrylic acid, itaconic acid, fumaric acid, maleic acid; vinylaryl sulfonic acids; their anhydrides; and combinations thereof.

10. The copolymer of claim 9, wherein the anionic monomer is an ethylenically unsaturated carboxylic acid selected from the group consisting of methacrylic acid, acrylic acid, and combinations thereof.

11. The copolymer of claim 1, wherein the non-quaternized cationic monomer is selected from the following structure:

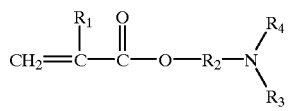
(A)

where
R$_1$=—H, —CH$_3$, or —CH$_2$CH$_3$,
R$_2$=—(CH$_2$—)$_n$, where n=1 to 40, linear or branched alkyl, cycloalkyl, aryl, a polyethylene oxide chain having the formula —(CH$_2$—CH$_2$—O)$_p$ where p=1 to 50, or a polypropylene oxide chain having the formula —(CH$_2$(CH$_3$)—CH$_2$—O—)$_p$ where p=1 to 50,
R$_3$, R$_4$, may be —H, —CH$_3$, —CH$_2$—CH$_3$, branched or linear alkyl, aryl, cycloalkyl, or combinations thereof.

12. The copolymer of claim 1, wherein the non-quaternized cationic monomer is selected from the non-quaternized group consisting of acrylamides, methacrylamides, acrylates, metliacrylates, vinyl amines, diallyl amines, vinyl heterocyclic amides, and combinations thereof.

13. The copolymer of claim 1, wherein the non-quaternized cationic monomer is selected from the non-quaternized group consisting of:
aromatic and aliphatic vinyl or allyl amines selected from the group consisting of vinyl amine, vinyl piridine, vinyl morpholine, vinyl imidazole, and their chloride, bromide, sulfate, sulfonate, phosphate, methyl and ethyl sulfonate salts; and
diallyl amines having the following structure:

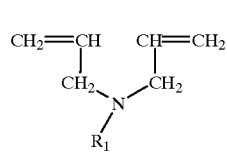
(A)

where R$_1$ may be: —H, —CH$_3$, —CH$_2$—CH$_3$, branched or linear alkyl, aryl, cycloalkyl, or combinations thereof.

14. The copolymer of claim 1 wherein the non-ionic hydrophilic monomer is selected from the group consisting of:

1) acrylates and methacrylates selected from the group consisting of hydroxyethyl methacrylate, hydroxyethyl acrylate, hydroxypropyl acrylate, hydroxyethyl acrylate, hydroxypropyl acrylate, methoxy-polyethylene-oxide methacrylate, and methoxy-polyethylene-oxide methacrylates of the structure:

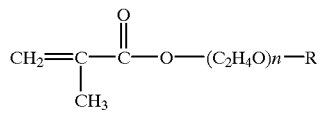

n is an integer from 1 to 100 and R is selected from the group consisting of H, OH, methyl, ethyl, lauryl, stearyl, carboxy, and amino groups, and combinations thereof, 2) ethylenically unsaturated amides having the following formula:

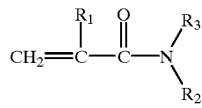

where R$_1$ is —H, —CH$_3$, —CH$_2$CH$_3$, and
where R$_1$ and R$_2$ are selected from the group consisting of H, OH, methyl, methylol, ethyl, lauryl, stearyl, carboxy, and amino groups, and combinations thereof, in particular, the groups consisting of acrylamide, methacrylamide, methyl acrylamide, dimethyl acrylamide, fumaramide, diacetone acrylamide, dimethyl methacrylamide;

3) cyclic amides having the following structure:

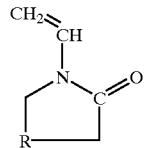

where R is an alkylene group such as —[CH$_2$—]$_n$, n=1 to 4, such as vinyl pyrrolidone (n=1), vinyl caproclactam (n=2), and 4) combinations thereof.

15. The copolymer of claim 1, wherein the non-ionic monomer is selected from the group consisting of 2-hydroxyethyl methacrylate, 2-hydroxyethyl acrylate, methacrylamide, vinyl pyrrolidone, hydroxypropyl methacrylate, and combinations thereof.

16. The copolymer of claim 1, wherein the hydrophobic monomer has the following structure:

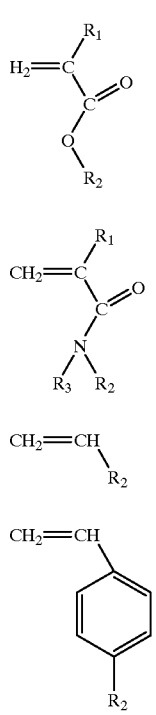

where
- $R_1$ is selected from hydrogen, methyl and ethyl groups,
- $R_2$ and $R_3$ is selected from alkyl groups having from 1 to 30, They can be linear or branched,
- $R_2$ and $R_3$ can also be selected from hydrogen or methoxy terminated oxyethylene and oxypropylene groups with structure:

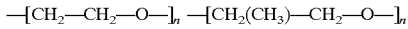

where n is an integer from 1 to 100.

17. The copolymer of claim 16, wherein the hydrophobic monomer is selected from the group consisting of higher alkyl esters of α,β-ethylenically unsaturated carboxylic acids, ethyl half esters of maleic anhydride, diethyl maleate, alkyl esters derived from the reactions of alkanols having from 4 to 20 carbon atoms with ethylenically unsaturated carboxylic acids, alkylaryl esters of ethylenically unsaturated carboxylic acids, N-alkyl ethylenically unsaturated amides and derivatives thereof, α-olefins, vinyl alkylates wherein the alkyl has at least 8 carbons, vinyl alkyl ethers, N-vinyl amides, ar-alkylstyrenes, and combinations thereof, and wherein said hydrophobic monomer is present in an amount from 1.00 to 10 mole percent.

18. The copolymer of claim 16, wherein the hydrophobic monomer is selected from the group consisting of:
1) higher alkyl esters of α,β-ethylenically unsaturated carboxylic acids selected from the group, consisting of dodecyl acrylate, dodecyl methacrylate, tridecyl acrylate, tridecyl methacrylate, tetradecyl acrylate, tetradecyl methacrylate, octadecyl acrylate, octadecyl methacrylate;

2) ethyl half esters of maleic anhydride, or diethyl maleate;

3) alkyl esters derived from the reactions of alkanols having from 4 to 80 carbon atoms with ethylenically unsaturated carboxylic acids selected from the group consisting of acrylic acid, methacrylic acid, maleic anhydride, fumaric acid, itaconic acid and aconitic acid;

4) alkylaryl esters of ethylenically unsaturated carboxylic acids selected from the group consisting of nonyl-α-phenyl acrylate, nonyl-α-phenyl methacrylate, dodecyl-α-phenyl acrylate, and dodecyl-α-phenyl methacrylate;

5) N-alkyl, ethylenically unsaturated amides selected from the group consisting of N-octadecyl acrylamide, N-octadecyl methacrylamide, N,N-dioctyl acrylamide, and derivatives thereof;

6) α-olefins selected from the group consisting of octene-1, decene-1, dodecene-1 and hexadecene-1;

7) vinyl alkylates selected from the group consisting of vinyl laurate and vinyl stearate;

8) vinyl alkyl ethers selected from the group consisting of dodecyl vinyl ether and hexadecyl vinyl ether;

9) N-vinyl amides selected from the group consisting of N-vinyl lauramide and N-vinyl stearamide;

10) styrene, methyl styrene, t-butyl styrene; and 11) combinations thereof, and wherein the hydrophobic monomer is used in an amount of less than 2 mole percent.

19. The copolymer of claim 16, wherein the hydrophobic monomer is selected from the group consisting of alkyl esters of acrylic acid and methacrylic acid, N-alkyl acrylamides and N-alkyl methacrylamides, wherein the alkyl has from 8 to 20 carbon atoms; t-butyl styrene; and combinations thereof.

20. The copolymer of claim 16, wherein the hydrophobic monomer is selected from the group consisting of alkyl methacrylates, wherein alkyl has from 10 to 20 carbon atoms, and t-butyl styrene.

21. The copolymer of claim 16, wherein the hydrophobic monomer is selected from the group consisting of dodecyl methacrylate and N-dodecyl methacrylamide, hexadecyl methacrylate and N-hexadecyl methacrylamide.

22. The copolymer of claim 1, wherein the cross-linking monomer is represented by the formula:

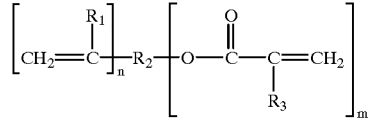

n, m=1 to 4, m+n≧2
$R_1$, $R_3$=H, alkyl
$R_2$=alkyl, cycloalkyl, aryl,
=—(CH$_2$—CH$_2$—O)$_p$— where p=1 to 50,
=—(CH$_2$(CH$_3$)—CH$_2$—O)$_p$— where p=1 to 50,
=amido, ester, polyamido, polyester.

23. The copolymer of claim 22, wherein the cross-linking monomer is selected from the group consisting of di-functional, tri-functional, and poly-functional monomers of vinyl, allyl, acrylic, methacrylic, acrylamido or methacrylamido, and combinations thereof.

24. The copolymer of claim 22, wherein the cross-linking monomer is selected from the group consisting of triallyl- 1,3,5-triazine-2,4,6(1H,3H,5H)-trione, ethylene glycol diacrylate, trimethylol, trimethacrylate propane triacrylate, trimethylol, trimethacrylate propane, allyl methacrylate, allyl citrate, di-allyl amine, tri-allyl amine, polyethylene glycol, di-acrylates, tri-acrylates, allyl pentaerythritol, allyl sucrose, methylenebisacrylamide, and combinations thereof.

25. The copolymer of claim 22, wherein the cross-linking monomer is selected from the group consisting of ethylene glycol dimethacrylate, allyl pentaerythritol, triallyl-1,3,5-triazine-2,4,6(1H,3H,5H)-trione, and trimethylol propane trimethacrylate.

26. The copolymer of claim 1, wherein the polymer is formed in the presence of a free radical initiator selected from the group consisting of azo-initiators, peroxo-initiators, and combinations thereof.

27. The copolymer of claim 26, wherein the initiator is a peroxo-initiator selected from the group consisting of lauryl peroxide, cumene hydroperoxide, ethyl hexyl peroxodicarbonate, diisopropyl peroxydicarbonate, 4-(t-butylperoxylperoxycarbonyl)-3-hexyl-6-7-(t-butyl peroxycarbonyl)heptyl cyclohexene (4-TBPCH), cumene hydroperoxide, t-butyl peroxyneodecanoate, t-butyl hydroperoxide, and benzoyl peroxide.

28. The copolymer of claim 26, wherein the initiator is an azo-initiator selected from the group consisting of azobis-dimethylvaleronitrile, azobis-isobutyronitrile, azobis-methylbutyronitrile, 2,2'-azobis (4-methoxy-2,4-dimethylvalenonitrile), 2,2'-azobis (2,4-dimethylvalenonitrile).

29. The copolymer of claim 26, wherein the initiator is 2,2'-azobis(2-methylbutyronitrile).

30. The copolymer of claim 1, wherein:
the anionic monomer is at a concentration of 2.0 to 20 mol % and is selected from the group consisting of acrylic acid and methacrylic acid;
the cationic monomer is at a concentration of 10 to 45 mol % and is selected from the group consisting of N-(dimethylaminoethyl) methacrylate and N-(dimethylaminopropyl) methacrylamide;
the non-ionic hydrophilic monomer is at a concentration of 15 to 94 mol % and is selected from the group consisting of hydroxyethyl methacrylate, hydroxyethyl acrylate, methacrylamide, N-vinyl pyrrolidone, hydroxy propyl methacrylate and combinations thereof;
the hydrophobic monomer is at a concentration of 2.0 to 5.0 mol % and is stearyl methacrylate; and,
the crosslinking monomer is at a concentration of about 0.90 mol %.

31. A hydroplilic ampholytic copolymer which is compatible with both anionic and cationic materials, the copolymer being formed by copolymerizing:
0.05 to 20 mol percent of an anionic monomer;
10 to 45 mol percent of a non-quaternized cationic monomer;
35 to 95 mol percent of a non-ionic hydrophilic monomer in a sufficient quantity to provide the copolymer with a glass transition temperature of above about 50° C.;
0.5 to 10 mol percent of a hydrophobic monomer; and,
0 to 1.5 mol percent of a cross-linking monomer.

32. A method of preparing a hydrophilic ampholytic polymeric copolymer comprising copolymerizing:
0.05 to 20 mol percent of an anionic monomer having at least one carboxy-functional group;
10 to 45 mol percent of a non-quaternized cationic monomer having at least one amino-functional group;
45 to 90 mol percent of a non-ionic hydrophilic monomer;
0.5 to 10 mol percent of a hydrophobic monomer; and
0 to 1.5 mol percent of a cross-linking monomer,
wherein the monomers are selected so as to provide the copolymer with a glass transition temperature of above about 50° C. and the non-quaternized cationic monomer to the anionic monomer ratio is from about 2:1 to about 16:1.

33. The method of claim 32 wherein the copolymerization is carried out in a copolymerization media which includes a solvent in which the monomers are soluble and the copolymer is insoluble.

34. The method of claim 32, wherein the copolymer is precipitated from a copolymerization media and wherein the monomers have solubility parameters that are less than or equal to 2 (MPa)$^{1/2}$ below a solubility parameter of the solvent.

35. The method of claim 32, wherein the solvent comprises at least two solvents and wherein the monomers have solubility parameters that are less than or equal to 2 (MPa)$^{1/2}$ below the combined solubility parameter of the solvents.

36. The method of claim 32, wherein the solvent is selected from the group consisting of saturated unbranched aliphatic hydrocarbons, including pentane, hexane, and heptane; saturated cyclic hydrocarbons, including cyclohexane; branched hydrocarbons; mineral spirits; mineral oils; ethers, including dimethyl ether, and diethyl ether; esters, including n-butyl acetate, t-butyl acetate, propyl acetate, ethyl acetate, and methyl acetate; unsaturated aromatic hydrocarbons, including benzene, toluene, and xylene; perfluorinated fluids including perfluorohexane, perfluorooctane, perfluoro alkyl ether, perfluoroalkyl amines, and trifluoro ethanol; alcohols, including t-butyl alcohol, isopropyl alcohol, methanol; methylene chloride; halogenated solvents; and combinations thereof.

37. The method of claim 32, wherein the copolymerization is initiated by a free radical initiator at a concentration of 0.005 to 1 mole percent.

38. The method of claim 32, further including:
adding a polymerization additive to minimize agglomeration of copolymer particles as they are formed.

39. The method of claim 32, wherein the copolymerization is conducted in the presence of a polymerization additive selected from the group consisting of nonionic surfactants with an equivalent hydrophobic/hydrophilic balance of from about 2:1 to about 16:1.

40. The method of claim 39, wherein the nonionic surfactant has an equivalent hydrophobic/hydrophilic balance of from about 2:1 to about 8:1.

41. The method of claim 39, wherein the nonionic surfactant is selected from the group consisting of:
1) alkyl polyethyleneoxy compounds represented by the formula, RO(EO)$_n$—H, wherein R is a C$_8$–C$_{18}$ alkyl, EO is ethyleneoxy and n is an integer from 1 to 10;
2) polysiloxane polyether copolymers selected from the group consisting of silicone glycols and dimethicone copolyols, and
3) non-ionic block copolymer surfactants.

42. The method of claim 39, wherein the polymerization additive is at a concentration of 0.001–26 weight %.

43. The method of claim 33, further including:
separating the solvent from the copolymer by evaporation.

44. A thickened aqueous formulation comprising:
water;
0.5–15% by weight based upon the total weight of the formulation of the copolymer of claim 1; and an effective amount of an acid sufficient to neutralize the copolymer; and, achieve a solution viscosity of at least about 1500 cP.

45. The formulation of claim 44, wherein the acid is an organic acid selected from the group consisting of citric acid, lactic acid, glycolic acid, salicilic acid, amino acids, or combinations thereof, and wherein the acid is at a concentration of about 0.05–30% by weight based upon the weight of the formulation.

46. A shampoo and conditioning formulation comprising cleaning and conditioning; the copolymer of claim 1; an organic acid to adjust the pH to about 4.5; and water.

47. A fabric softener comprising dimethyl dialkyl ammonium chloride; acetic acid; the copolymer of claim 1; fragrance; and water.

48. A composition for oral delivery of a medicament or active comprising the copolymer of claim 1; and a medicament or active.

49. A method of improving transport of an orally delivered medicament from a digestive system to a blood stream comprising combining the medicament with an amount of the hydrophilic ampholytic polymer of claim 1 and administering the medicament orally.

50. A method of removing phosphate from a patient comprising orally administering to said patient a therapeutically effective amount of a composition comprising at least one polymer of claim 1.

51. A method of lowering the concentration of a phosphate ion in the body, said method comprising administering to a subject an effective amount of a copolymer of claim 1.

52. A method of treating an undesirable condition in the body, said method comprising administering to such body a copolymer of claim 1 in combination with a cationic material or cationic polymer.

53. A method of modifying the rheology of a composition, said method comprising adding to such composition an effective amount of a copolymer of claim 1.

54. A pharmaceutical composition comprising a biologically active ingredient and an excipient containing a copolymer of claim 1.

* * * * *